(12) United States Patent
Ashihara et al.

(10) Patent No.: US 7,963,932 B2
(45) Date of Patent: Jun. 21, 2011

(54) APPARATUS FOR ASSISTING LIMB AND COMPUTER PROGRAM

(75) Inventors: Jun Ashihara, Saitama (JP); Yutaka Hiki, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 1420 days.

(21) Appl. No.: 11/444,374

(22) Filed: Jun. 1, 2006

(65) Prior Publication Data

US 2006/0276728 A1 Dec. 7, 2006

(30) Foreign Application Priority Data

Jun. 3, 2005 (JP) .................................. 2005-163864

(51) Int. Cl.
*A61H 1/00* (2006.01)
*A61F 5/00* (2006.01)

(52) U.S. Cl. .................................. 601/5; 601/35; 602/23
(58) Field of Classification Search ................ 601/5, 23, 601/33, 34, 35; 623/24, 27; 602/16, 19, 602/23, 26, 27; 482/4, 51, 66
See application file for complete search history.

(56) References Cited

U.S. PATENT DOCUMENTS

| 4,557,257 | A | 12/1985 | Fernandez et al. |
| 5,020,790 | A | 6/1991 | Beard et al. |
| 6,666,796 | B1 * | 12/2003 | MacCready, Jr. ............... 482/66 |
| 6,872,187 | B1 | 3/2005 | Stark et al. |

FOREIGN PATENT DOCUMENTS

| EP | 0 380 060 A2 | 8/1990 |
| JP | 05-329186 | 12/1993 |
| JP | 2003-220102 | 8/2003 |
| JP | 2004-329520 | 11/2004 |

* cited by examiner

*Primary Examiner* — Quang D Thanh
(74) *Attorney, Agent, or Firm* — Squire, Sanders & Dempsey (US) LLP

(57) ABSTRACT

An apparatus for assisting limb includes a body attachment, a link for upper leg, and a knee joint unit, a link for lower leg, a lower limb attachment, a drive unit and a knee joint actuator. The body attachment is attached to a trunk of a user. The link for upper leg is placed alongside with an upper leg of the user and coupled with the body attachment. The link for lower leg is placed alongside with a lower leg of the user and coupled with the link for upper leg via the knee joint unit. The lower limb attachment is attached to one of the lower leg and a foot of the user, and coupled with the link for lower leg. The knee joint actuator is placed in the body attachment so as to apply rotational torque to the knee joint unit via the drive unit.

19 Claims, 25 Drawing Sheets

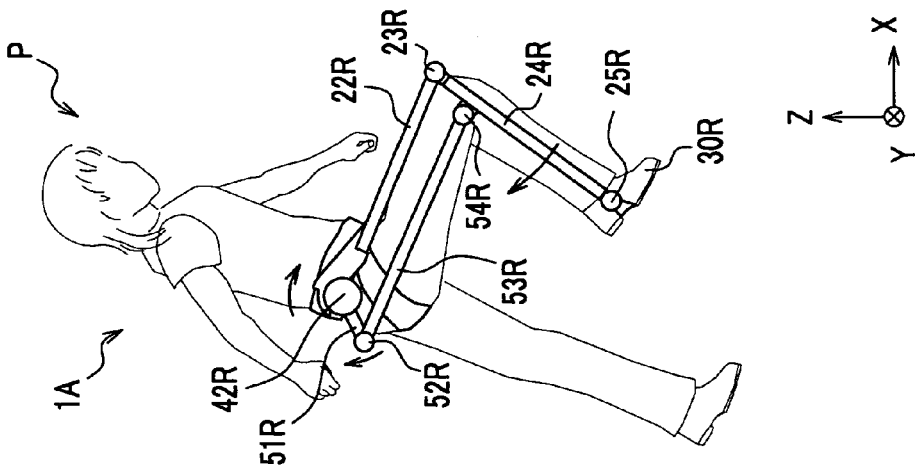
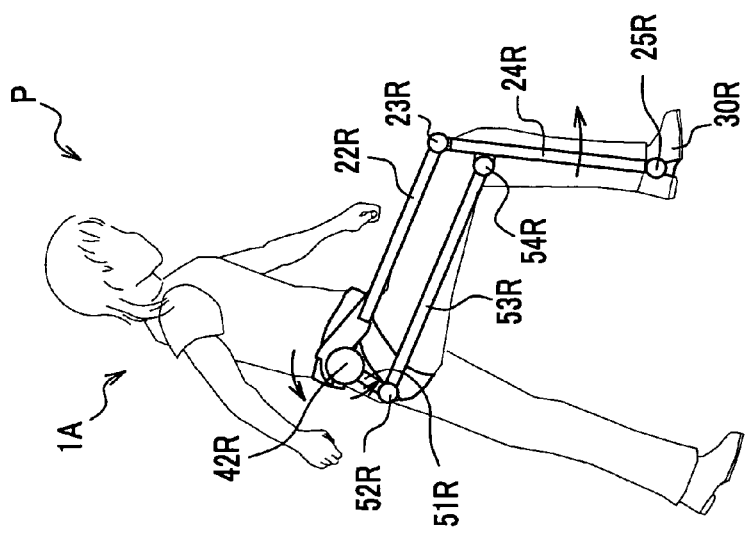
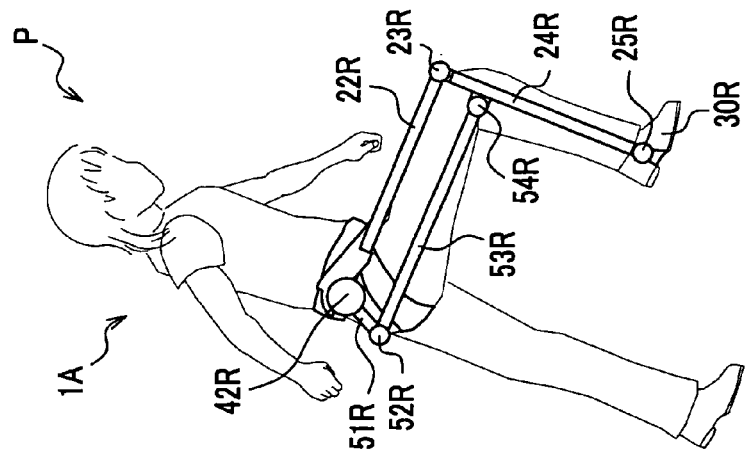

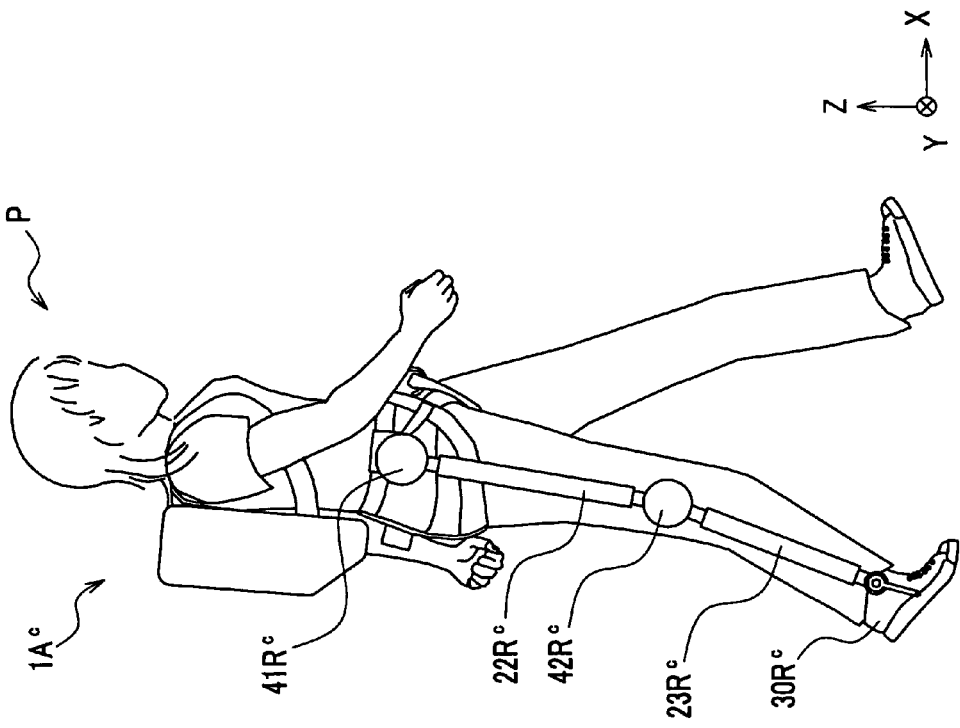
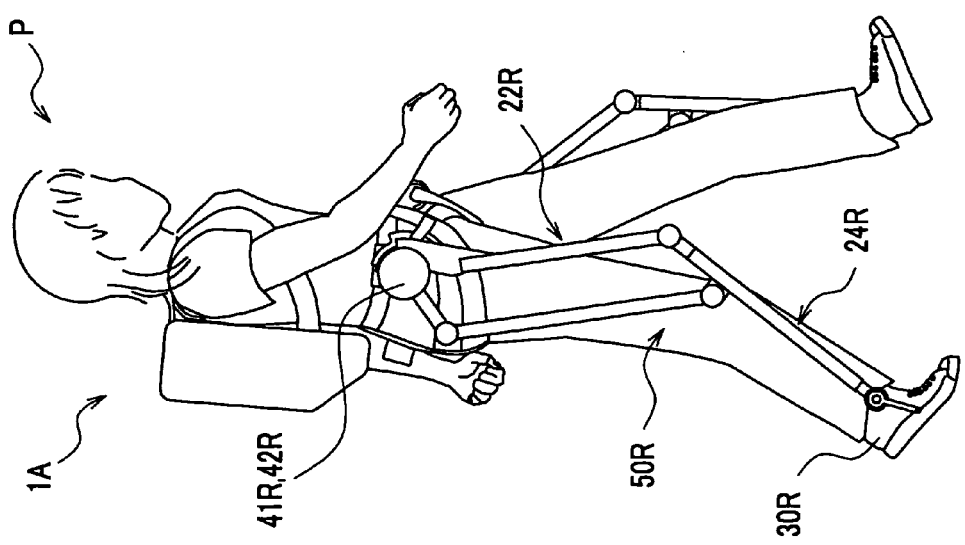

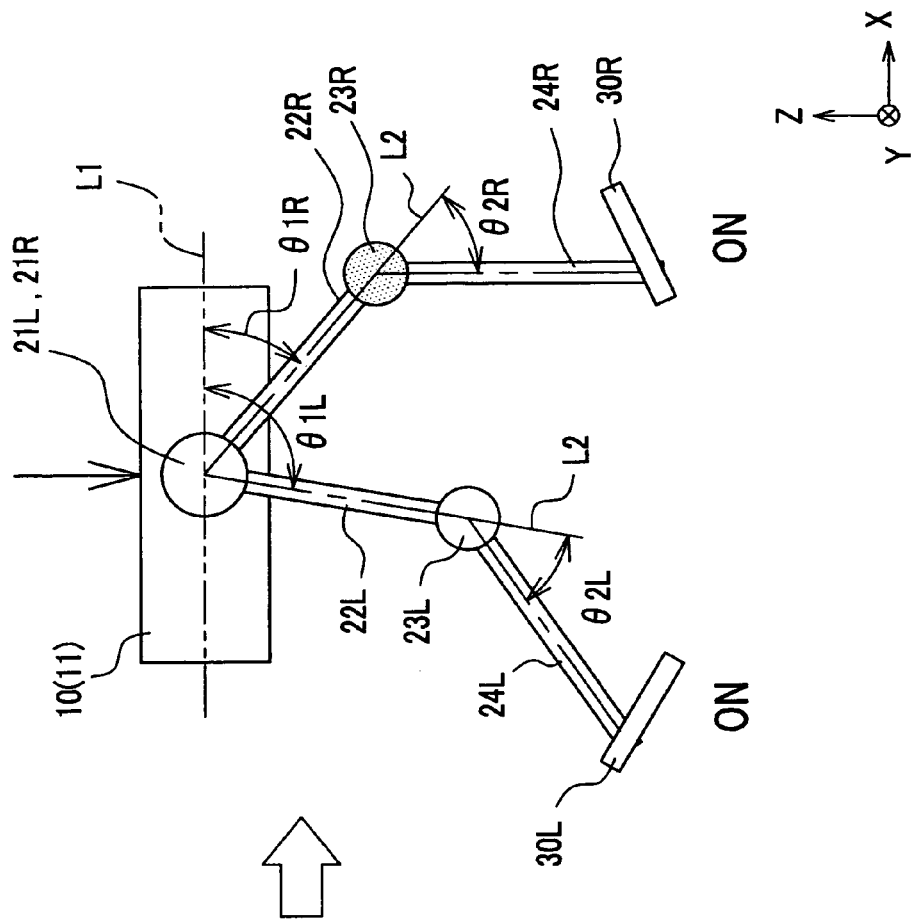
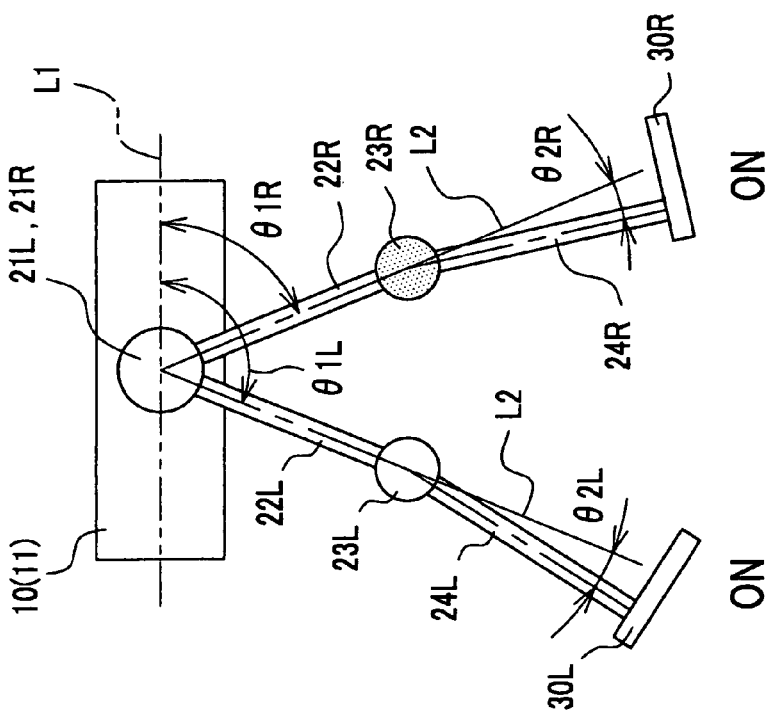
FIG. 12A
FIG. 12B

STATE 1

STATE 2

STATE 3

STATE 4

STATE 5

STATE 6

STATE 7(STATE 1)

FIG.26
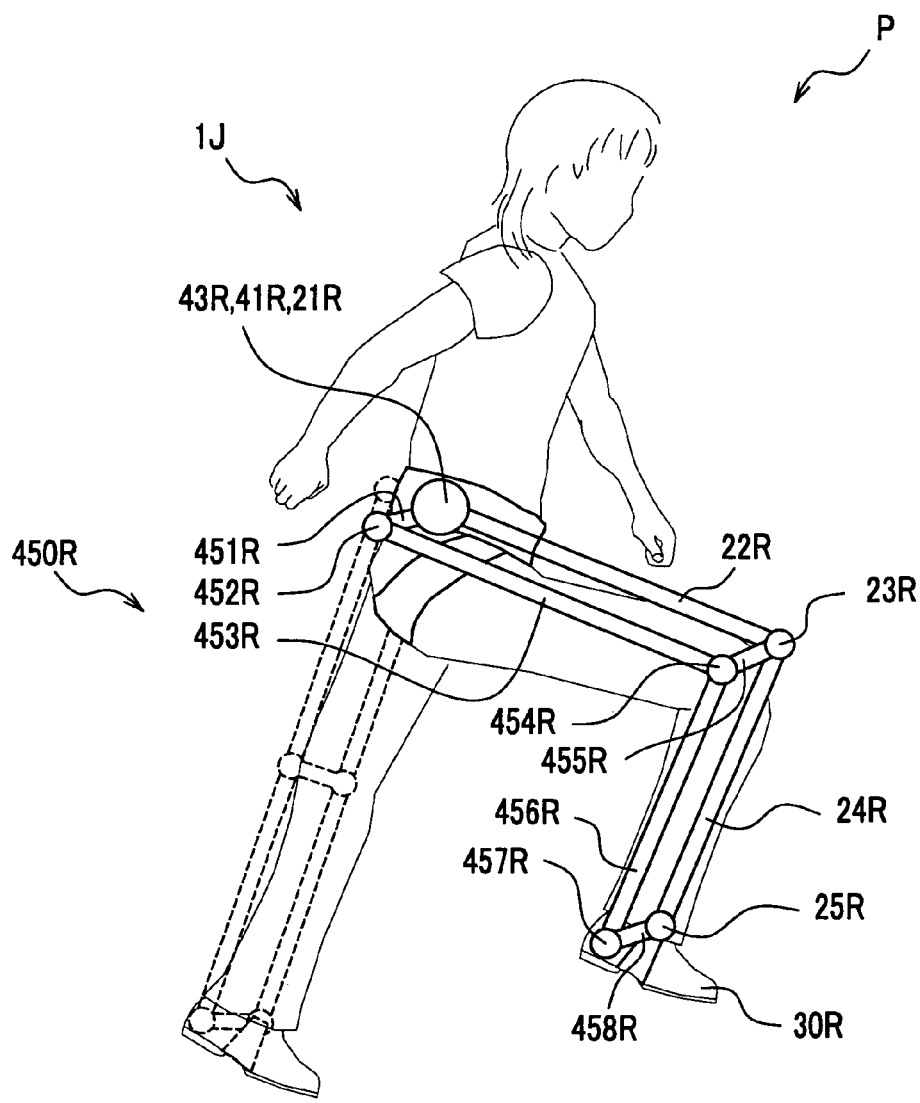
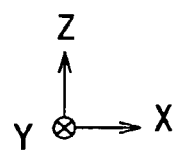

APPARATUS FOR ASSISTING LIMB AND COMPUTER PROGRAM

BACKGROUND OF THE INVENTION

The present invention relates to an apparatus for assisting limb and a computer program for executing a computer for the apparatus.

Walk-assisting devices which are designed to provide an assist force required for a user in walking have been disclosed in recent years. A walk-assisting device is typically used by a person who has difficulty in walking by himself, such as one lost muscle strength or suffering from leg injury. In addition, it is anticipated that a walk-assisting device will be applied to exercise and amusement, aiming at improvement in muscle strength and walking posture.

A patent document 1 discloses a walk-assisting device which is attached to a lower limb of a user and has joint actuators (actuator: a combination of an electric motor and reduction gears), which are placed coaxially with a hip joint, a knee joint and an ankle joint of the user, respectively, so as to rotate them, so that the walk-assisting device provides the user with a certain drive force. Patent document 1: Japanese Published Patent Application H05-329186 (paragraphs 0034-0036, FIG. 15 and FIG. 16)

However, the walk-assisting device described in the patent document 1 has a problem that because the device has supporting members which tightly restrict a whole lower limb of a user, there is a great inertial moment resulting from movement of the lower limb. Generally speaking, it is necessary that a walk-assisting device should drive supporting members synchronously with movement of a lower limb of a user. If a great inertial moment occurs, it may be possibly difficult to carry out synchronous control due to response delay of the supporting members.

If an actuator having sufficient capacity is adopted for a joint driving unit so as to cancel an adverse effect due to a great inertial moment, the joint driving unit results in a large-size one, which consumes a great amount of power.

In addition, a great inertial moment leads to degraded feeling and fatigue of a user wearing a walk-assisting device.

The walk-assisting device described in the patent document 1, in which a whole lower limb of a user is tightly restricted by support members and the user needs to support total weight including his self weight and the walk-assisting device, he tends to experience uncomfortably restrictive feeling, pain and feeling of a high load Because the walk-assisting device restricts a whole lower limb with support members, it is necessary that the support members should be a custom-built model so that the device is compatible with his figure and habit in walking.

SUMMARY OF THE INVENTION

In view of the background described above, the present invention has been developed, which provides an apparatus for assisting limb able to reduce an inertial moment applied to a user.

The apparatus according to the present invention, which has flexibility for various types of users, is able to reduce not only restriction but also load for a lower limb of a user with light-weight arrangement.

The present invention also provides a computer program, which executes a computer to control the apparatus.

It is an aspect of the present invention to provide an apparatus for assisting limb including a body attachment, a link for upper leg, a knee joint unit, a link for lower leg, a lower limb attachment, a drive unit and a knee joint actuator. The body attachment is attached to a trunk of a user. The link for upper leg is placed alongside with an upper leg of the user and coupled with the body attachment. The link for lower leg is placed alongside with a lower leg of the user and coupled with the link for the upper leg via the knee joint unit. The lower limb attachment is attached to one of the lower leg and a foot of the user, and coupled with the link for lower leg. The knee joint actuator is placed in the body attachment so as to apply rotational torque to the knee joint unit via the drive unit.

The trunk of the user described above is meant to represent a shoulder, a chest, a back, an abdomen, a waist and a hip of the user.

Because the knee joint actuator which has remarkably great weight in the apparatus for assisting limb is located in the trunk of the user, it is possible to reduce an inertial moment applied to the user during movement of a limb, which results from the weight of the knee joint actuator. The apparatus for assisting limb, which reduces the inertial moment applied to the user, is able not only to improve feeling of the user wearing the apparatus, but also to restrain fatigue experienced by the user.

It is another aspect of the present invention to provide an apparatus for assisting limb further including a foot detector and a controller. The foot detector is configured to detect one of a landed phase and a lifted phase of the foot of the user. The controller is configured to control the knee joint actuator. The lower limb attachment is attached to the foot of the user so that the lower limb attachment is able to land on the ground. The controller performs drive control for the knee joint actuator so as to provide an assist force freeing the user from weight via the lower limb attachment in a landed phase, the link for lower leg, the link for upper leg, the drive unit and the body attachment.

A landed phase occurs when a reaction force from a floor is exerted on a foot of a user. In other words, it is meant to represent not only a case where the foot of the user directly lands on the floor but also a case where a shoe worn by the user lands on the floor. In contrast, a lifted phase occurs when the reaction force from the floor is not exerted on the foot of the user. By detecting landed and lifted phases, it is possible to generate an assist force only when necessary.

An assist force is meant to represent a force supporting a part of the weight of the user. By providing this force, it is possible to reduce a load imposed on the user. In this connection, weight is meant to represent net weight adding up body weight, clothing and personal effects, which should be supported by lower limbs of the user when he does not use an apparatus for assisting limb.

In this way, it is possible to provide the apparatus for assisting limb, which is able to reduce not only restriction but also a load applied to the lower limb.

It is still another aspect of the present invention to provide an apparatus for assisting limb, in which the controller terminates driving of the knee joint actuator when the foot detector detects a lifted phase.

It is possible to prevent the apparatus described above from obstructing a lifted lower limb of the user.

It is yet another aspect of the present invention to provide an apparatus for assisting limb, in which the assist force is equal to one of a predetermined value and a certain percentage of the weight of the user.

The apparatus described above is able to perform control for the actuator according to purposes, providing a desired assist force to the user.

It is a further aspect of the present invention to provide an apparatus for assisting limb further including a load detector which detects a load imposed by the user via the body attachment on the link for upper leg, the link for lower leg, the drive unit and the lower limb attachment. The controller performs drive control for the knee joint actuator in a landed phase based on the load detected by the load detector.

The load detected by the load detector corresponds to an assist force applied by the apparatus for assisting limb. Accordingly, it is possible to carry out feedback control with the current assist force.

It is a still further aspect of the present invention to provide an apparatus for assisting limb, in which the assist force has a lower limit and an upper limit and the controller performs drive control for the knee joint actuator in a landed phase based on the load detected by the load detector so that the assist force exists between the lower and upper limits.

When the load detected by the load detector is less than the lower limit, the controller in the apparatus described above drives the actuator so as to increase the load. When the load detected by the load detector is not less than the lower limit, in contrast, the controller drives the actuator so as to decrease the load. In this way, it is possible to perform control for the actuator so as to apply an assist force in an appropriate range.

It is a yet further aspect of the present invention to provide an apparatus for assisting limb further including a behavior detector, which is configured to detect a signal indicative of behavior for the link for upper leg and the link for lower leg. The controller performs drive control for the knee joint actuator based on the signal detected by the behavior detector.

A rotary encoder detecting a rotational angle of the actuator is an example of the behavior detector. Because the behavior detector is able to control an amount of driving of the actuator according to the behavior of the apparatus for assisting limb, it is possible to provide an assist force, which does not have an adverse effect on the posture of a user.

It is another aspect of the present invention to provide an apparatus for assisting limb, in which a first portion at which the assist force is applied to the user via the link for upper leg and a second portion to which the load of the user is applied in the body attachment are positioned so that the first and second portions are substantially included in a common vertical plane.

The vertical plane described above is a plane which is vertical with respect to a floor. The apparatus is able to prevent an undesirable inertial moment in a pitch direction (about Y-axis) applied to a user.

It is still another aspect to provide an apparatus for assisting limb further including a hip joint unit and a hip joint actuator. The body attachment is coupled with the link for upper leg via the hip joint unit. The hip joint actuator is integrally installed with the knee joint actuator in the body attachment so as to apply rotational torque to the hip joint unit.

It is yet another aspect of the present invention to provide an apparatus for assisting limb, which further includes a foot detector and a controller. The foot detector is configured to detect one of a landed phase and a lifted phase of the foot of the user. The controller is configured to control the knee joint actuator and the hip joint actuator. The lower limb attachment is attached to the foot of the user so that the lower limb attachment is able to land on the ground. The controller performs drive control for the knee joint actuator and the hip joint actuator so as to provide an assist force freeing the user from weight via the lower limb attachment in a landed phase, the link for lower leg, the link for upper leg, the drive unit and the body attachment.

Because the knee joint actuator having larger weight is integrally placed with the hip joint actuator, it is possible to decrease a load imposed on the hip joint actuator. This leads to miniaturization and a reduction in power consumption for the hip joint actuator.

It is a further aspect of the present invention to provide an apparatus for assisting limb, in which when the foot detector detects a lifted phase, the controller terminates driving of at least one of the knee joint actuator and the hip joint actuator.

It is a still further aspect of the present invention to provide an apparatus for assisting limb, in which when the foot detector detects a lifted phase, the controller performs drive control for the hip joint actuator so as to assist a swing for the upper leg of the user.

The apparatus described above is able to provide assist for swing of a lifted lower limb of a user.

It is yet further aspect of the present invention to provide a computer program for an apparatus for assisting limb. The apparatus includes a controller, a body attachment, a link for upper leg, a knee joint unit, a link for lower leg, a lower limb attachment, a drive unit, a knee joint actuator and a foot detector. The body attachment is attached to a trunk of a user. The link for upper leg is placed alongside with an upper leg of the user and coupled with the body attachment. The link for lower leg is placed alongside with a lower leg of the user and coupled with the link for the upper leg via the knee joint unit. The lower limb attachment is attached to a foot of the user so as to land on the ground and coupled with the link for lower leg. The knee joint actuator is placed in the body attachment so as to apply rotational torque to the knee joint unit via the drive unit. The foot detector is configured to detect one of a landed phase and a lifted phase of the foot of the user. The computer program executes the controller in a process including performing drive control for the knee joint actuator so as to provide an assist force freeing the user from weight via the lower limb attachment in a landed phase, the link for lower leg, the link for upper leg, the drive unit and the body attachment.

It is another aspect of the present invention to provide a computer program for an apparatus for assisting limb. The apparatus includes a controller, a body attachment, a hip joint unit, a link for upper leg, a knee joint unit, a link for lower leg, a lower limb attachment, a drive unit, a knee joint actuator, a hip joint actuator and a foot detector. The body attachment is attached to a trunk of a user. The link for upper leg is placed alongside with an upper leg of the user and coupled with the body attachment via the hip joint unit. The link for lower leg is placed alongside with a lower leg of the user and coupled with the link for the upper leg via the knee joint unit. The lower limb attachment is attached to a foot of the user so as to land on the ground and coupled with the link for lower leg. The knee joint actuator is placed in the body attachment so as to apply rotational torque to the knee joint unit via the drive unit. The hip joint actuator is integrally installed with the knee joint actuator in the body attachment so as to apply rotational torque to the hip joint unit. The foot detector is configured to detect one of a landed phase and a lifted phase of the foot of the user. The computer program executes the controller in a process including performing drive control for the knee joint actuator and the hip joint actuator so as to provide an assist force freeing the user from weight via the lower limb attachment in a landed phase, the link for lower leg, the link for upper leg, the drive unit and the body attachment.

BRIEF DESCRIPTION OF THE DRAWINGS

FIGS. 9A to 9C are each a schematic diagram illustrating movement of an apparatus for assisting limb.

FIG. 10A is a schematic diagram illustrating inertial moment in an apparatus for assisting limb. FIG. 10B is a schematic diagram illustrating inertial moment in a conventional apparatus.

FIG. 12A is a schematic diagram illustrating a direction of torque when sufficient torque is given. FIG. 12B is a schematic diagram illustrating a direction of torque when insufficient torque is given and the hip of a user is going to fall.

FIG. 26 is a side view illustrating a modification of an apparatus for assisting limb.

DESCRIPTION OF THE PREFERRED EMBODIMENTS

Embodiments of the present invention is now be described with reference to the drawings, showing an example in which an apparatus for assisting limb according to the present invention is applied to a lower limb of a user. Giving a common symbol to similar elements, description will not be repeated for these elements. In the following description coordinates are selected, which have X-axis oriented in forward and backward directions, Y-axis oriented in right and left directions and Z-direction oriented in upward and downward directions with respect to the user. Also standing posture of the user is selected as a reference. When a description is given of a member which has a counterpart in terms of right and left directions, such as a link for leg, right and left components are represented with symbols R (right) and L (left), respectively, as viewed from a user P, if it is necessary to distinguish these two members. If it is not necessary, description will be given without R or L.

I. First Embodiment

Figure 7:
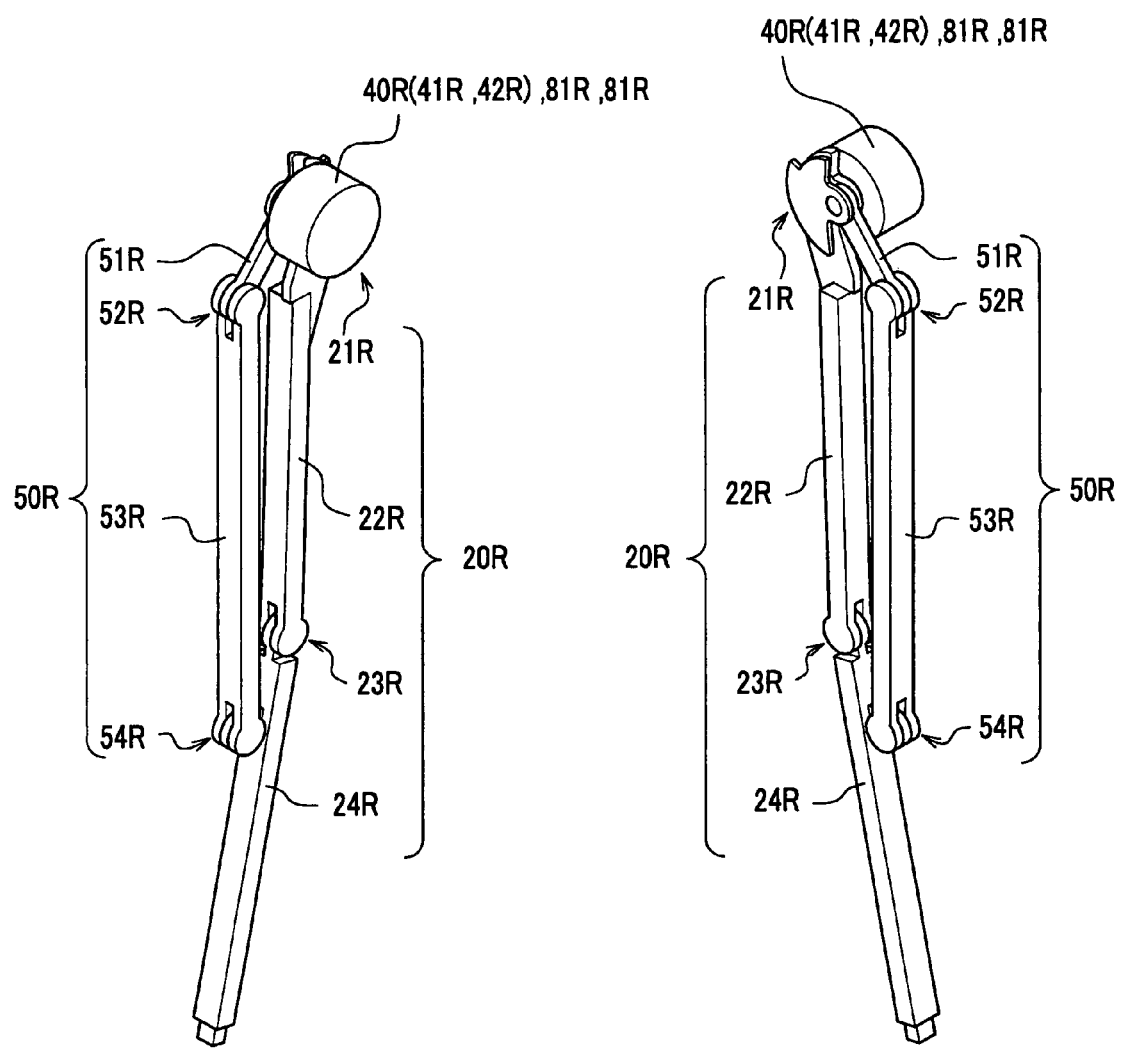
FIG. 7 is a perspective view showing a link for lower limb and a drive unit.

Description is given of an apparatus for assisting limb according to a first embodiment of the present invention. In FIG. 7 an ankle joint unit is not shown. FIG. 1 to FIG. 4 illustrate a user P who wears an apparatus 1A for assisting limb. For convenience of explanation, wires connecting actuators, sensors, controllers and batteries are not shown.

As shown in FIG. 1 to FIG. 4, the apparatus 1A for assisting limb (also referred to as "apparatus for assisting lower limb") includes a body attachment 10, links for lower limb 20L and 20R, foot attachments 30L and 30R, actuator units 40L and 40R, drive units 50L and 50R and a back pack BP.

a. Body Attachment 10

As shown in FIG. 1 to FIG. 4, the body attachment 10 (also referred to as "body trunk attachment") is attached to a trunk of the user P.

Figure 5A:
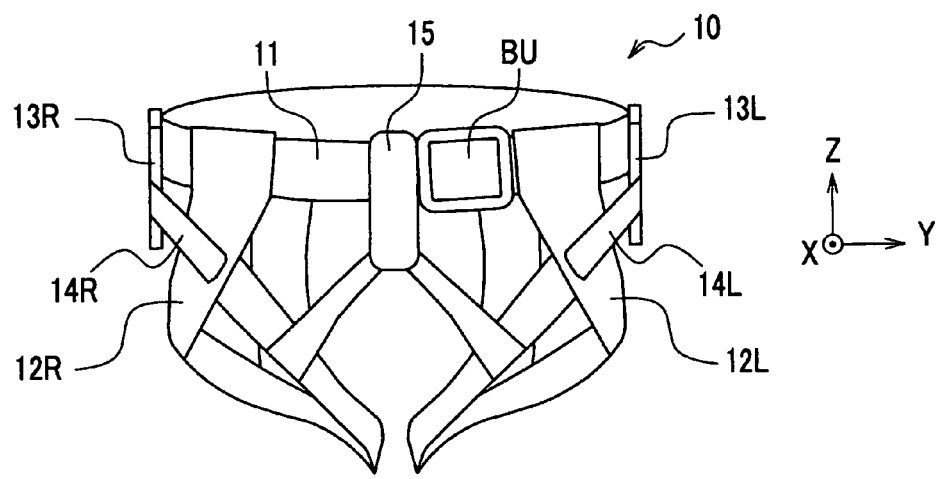
FIG. 5A is a front view illustrating a body attachment.
Figure 5B:
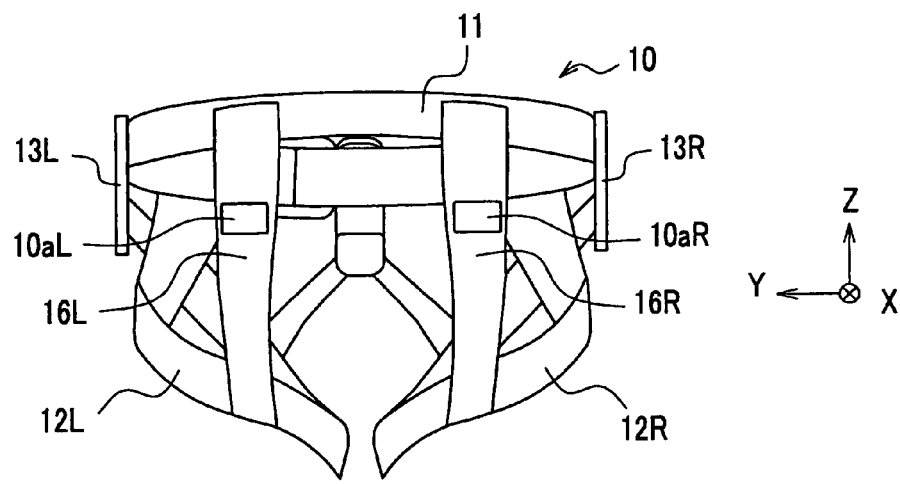
FIG. 5B is a rear view illustrating the body attachment.
Figure 5C:
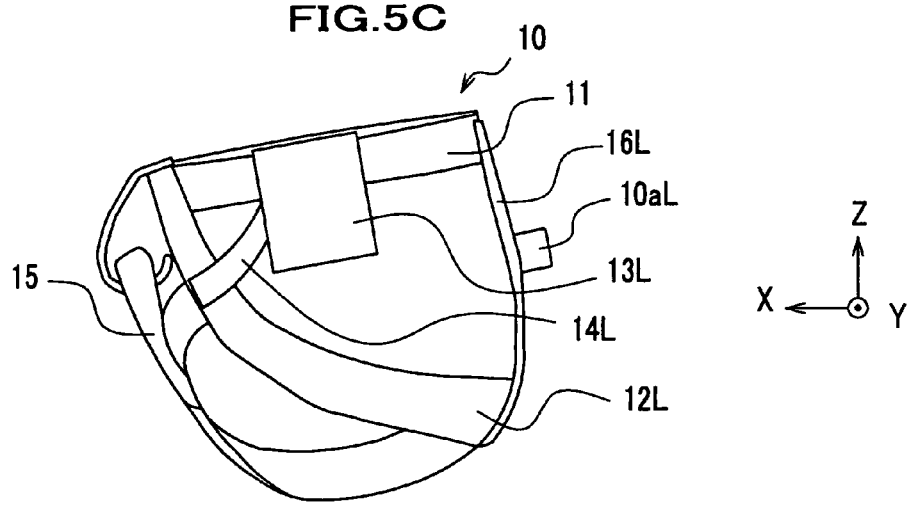
FIG. 5C is a side view illustrating the body attachment.

As shown in FIG. 5, the body attachment 10 includes a waist belt 11, upper leg belts 12L and 12R, actuator mounting members 13L and 13R, reinforcement members 14L and 14R and anti-loosening belts 15, 16L and 16R.

The waist belt 11, which is a cloth member attached around a waist of the user P, is able to adjust its length while worn by the user P by selecting an engagement position with a buckle BU.

An upper distal portion of the upper leg belt 12L (12R), which is made of a cloth member and attached around an upper leg of the user P, is secured to the waist belt 11.

The actuator mounting members 13L and 13R, which are each made of a plastic member configured to provide a place for mounting the actuator units 40L and 40R (see FIG. 1), are located opposite to each other on left and right sides of the waist belt 11.

The reinforcement member 14L (14R), which is a plastic member coupling the upper leg belt 12L (12R) with the actuator mounting member 13L (13R), reinforces the actuator mounting member 13L (13R) so as not be twisted by reaction torque created by the actuator unit 40L (40R).

The anti-loosening belt 15, which is a cloth member coupling the upper leg belt 12L (12R) with the waist belt 11 at a front portion of the user P, prevents downward loosening of the upper leg belt 12L (12R).

The anti-loosening belt 16L (16R), which is a cloth member coupling the upper leg belt 12L (12R) with the waist belt 11 at a rear portion of the user P, prevents downward loosening of the upper leg belt 12L (12R).

In this connection, it may be alternatively possible to adopt a waist belt 11 and upper leg belts 12L and 12R made of plastic. It may be alternatively possible to adopt actuator mounting members 13L and 13R and reinforcement members 14L and 14R made of metal. Furthermore, it may be alternatively possible to adopt anti-loosening belts 15, 16L and 16R made of plastic or metal.

Load sensors 10aL and 10aR are attached to the anti-loosening belts 16L and 16R, respectively.

The load sensor 10aL (10aR), which is an example of "load detector" in the appended claims, detects a load imposed by the user P via the body attachment 10 on the link for lower limb 20L (20R) and the drive unit 50L (50R). When the apparatus 1A for assisting limb supports a part of weight of the user P, the waist belt 11 is supported by the links for lower limb 20L and 20R, the foot attachments 30L and 30R and the drive units 50L and 50R. Since a part of the weight of the user P is imposed, on the other hand, on the upper leg belts 12L and 12R, a tensile force in Z-axis direction, which is produced by the waist belt 11 and the upper leg belts 12L and 12R, occurs in each of the anti-loosening belts 16L and 16R. Detecting this tensile force, the load sensor 10aL (10aR) detects a load imposed by the user P on the link for lower limb 20L (20R).

It may be preferable, but not necessarily, to use a unit with a load cell, a strain gauge or a piezoelectric element for the load sensors 10aL and 10aR. The load sensor 10aL (10aR) described above as an example is a type of one axis (Z-axis) detection, but it may be alternatively possible to use a sensor having two or more axes of detection so as to more accurately detect a load imposed by the user P on the link for lower limb 20L (20R) and the drive unit 50L (50R). In addition, it may be possible to attach a load sensor at a front portion of the anti-loosening belt 15 or at a portion of the body attachment 10 under a crotch of the user P so as to detect a pressure applied by the user P.

b. Links for lower limb 20L and 20R

As shown in FIG. 1 to FIG. 4 and FIG. 7, the link for lower limb 20L (20R), which is placed alongside with a leg (lower limb) of the user P, couples the body attachment 10 and the foot attachment 30L (30R) via a plurality of joint units.

The link for lower limb 20L (20R) includes a hip joint unit 21L (21R), a link for upper leg 22L (22R), a knee joint unit 23L (23R), a link for lower leg 24L (24R) and an ankle joint unit 25L (25R).

The hip joint unit 21L (21R) is placed outside of a hip joint of the user P. The hip joint unit 21L (21R) couples the link for upper leg 22L (22R) and the waist belt 11 so that the link for upper leg 22L (22R) is rotatable about Y-axis with respect to the waist belt 11.

The link for upper legs 22L (22R) is a link extending along an outer side of an upper leg of the user P. An upper distal portion of the link for upper leg 22L (22R) is coupled with the hip joint unit 21L (21R). A lower distal portion of the link for upper leg 22L (22R) is coupled with the knee joint unit 23L (23R).

The knee joint unit 23L (23R), which is located outside of a knee joint of the user P, rotatably couples the link for upper leg 22L (22R) with the link for lower leg 24L (24R).

It may be possible to position each of the knee joint units 23L and 23R so that its rotational axis is aligned coaxially with or in parallel with that of a knee joint of the user P.

The link for lower leg 24L (24R) is a link extending along an outer side of a lower leg of the user P.

An upper distal portion of the link for lower leg 24L (24R) is coupled with the knee joint unit 23L (23R). A lower distal portion of the link for lower leg 24L (24R) is coupled with the ankle joint unit 25L (25R).

The ankle joint unit 25L (25R) couples the link for lower leg 24L (24R) and the foot attachment 30L (30R) rotatably about Y-axis. The ankle joint units 25L and 25R each move synchronously with movement of an ankle joint of the user P without obstructing the user P in walking.

c. Foot Attachments 30L and 30R

Figure 6B:
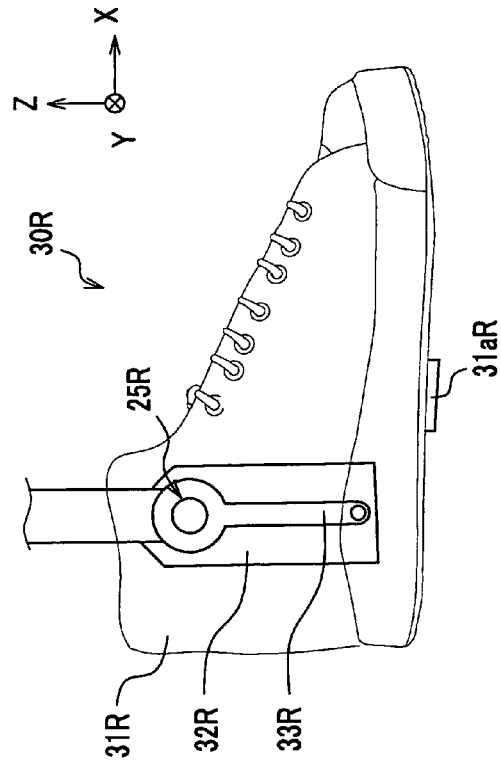
FIG. 6B is a side view illustrating the foot attachment.
Figure 6C:
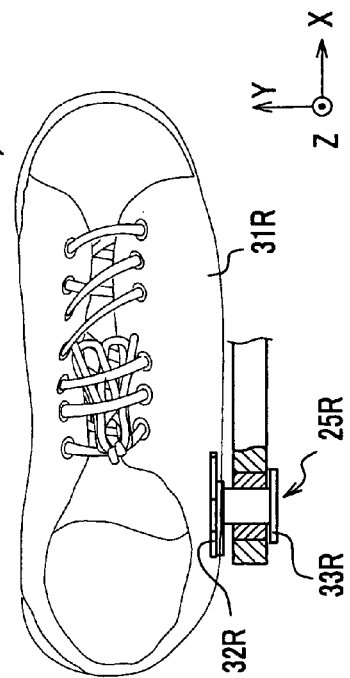
FIG. 6C is a plan view illustrating the foot attachment.
Figure 6A:
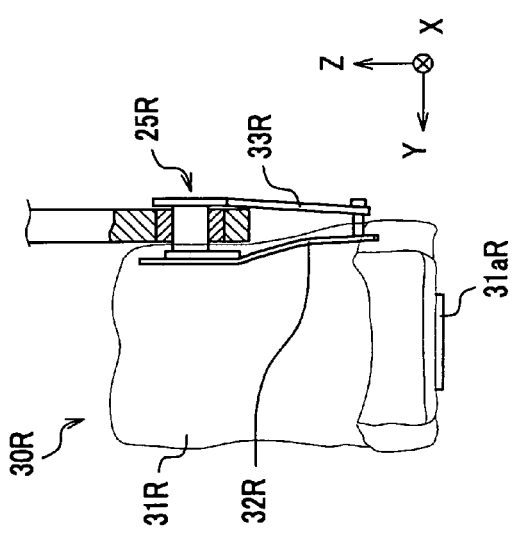
FIG. 6A is a rear view illustrating a foot attachment.

As shown in FIG. 1 to FIG. 4, the foot attachments 30L and 30R are each attached to a foot (distal portion of a lower limb) of the user P, which is an example of "lower limb attachment" shown in the appended claims. As shown in FIG. 6, the foot attachment 30L (30R) has a shoe unit 31L (31R), a reinforcement plate 32L (32R) and a support member 33L (33R). FIG. 6 shows the right foot attachment 30R, which is attached to a right foot of the user P. A figure is omitted for the left foot attachment 30L, which is mirror-symmetrical with the right foot attachment 30R.

The shoe units 31L and 31R are a pair of shoes which is attached to feet of the user P in such a manner that they are able to land on a floor.

The reinforcement plate 32L (32R), which is made of a plastic member placed along an outer side of a foot of the user P, is configured to transfer a reaction force, which is applied to the shoe unit 31L (31R) by the floor, to the link for lower limb 20L (20R) when the foot of the user P has landed on the ground. The shoe unit 31L (31R), the reinforcement plate 32L (32R) and the support member 33L (33R) are able to rotationally move in one united body with respect to the link for lower leg 24L (24R) via the ankle joint unit 25L (25R).

The support member 33L (33R) is a plastic member supporting the ankle joint unit 25L (25R) in collaboration with the reinforcement plate 32L (32R).

It may be possible to adopt reinforcement plates 32L and 32R and support members 33L and 33R made of metal.

In this embodiment, the links for lower limb 20L and 20R, the foot attachments 30L and 30R and the drive units 50L and 50R are each structurally configured to support a part of weight of the user P transferred to each of them via the body attachment 10.

Landing sensors 31aL and 31aR are attached to soles of the shoe units 31L and 31R, respectively. The landing sensors 31aL and 31aR each send an ON-signal to a controller 60 (see FIG. 11) while landed on the ground.

The landing sensor 31aL (31aR), which is intended to detect in which phase, a landed phase or a lifted phase, the foot attachment 30L (30R) is, is attached to the sole of the shoe unit 31L (31R) in this embodiment. These landing sensors 31aL and 31aR are each an example of "foot detector" shown in the appended claims.

The floor is not limited to a floor of a building but it may include a plane, such as the ground, on which the foot attachments 30L and 30R land when the user wearing the apparatus 1A for assisting limb moves (walks).

It may be preferable, but not necessarily, that a unit employing an electrically conductive rubber switch, a piezoelectric element or a strain gauge is selected for the landing sensors 31aL and 31aR. The landing sensors 31aL and 31aR are each one-axis sensor, but it may be alternatively possible to adopt a landing sensor able to detect two or more axial data.

When the landing sensor 31aL (31aR) generates an output, it means that the sensor 31aL (31aR) is detecting a landed phase. Otherwise, it is detecting a lifted phase.

In this embodiment, the landing sensor 31aL (31aR) is attached to a central portion of the sole of the shoe unit 31L (31R), but it may be alternatively possible to attach it to a different portion of the sole, such as a heel. Also it may be possible that a plurality landing sensors 31aL (31aR) are attached to the shoe unit 31L (31R).

In this embodiment, a member of aluminum alloy is applied to each of the links for upper leg 22L and 22R, the links for lower leg 24L and 24R, first links 51L and 51R and second links 53L and 53R, it may be alternatively possible that each is made of other material excelling in light weight and strength, carbon fiber reinforced plastic, for example.

d. Actuator unit 40L and 40R

The actuator unit 40L (40R), which is, as shown in FIGS. 1 to 4, attached to the actuator mounting member 13L (13R) (see FIG. 5), has a hip joint actuator 41L (41R) and a knee joint actuator 42L (42R).

The hip joint actuator 41L (41R) has an electric motor and reduction gears, which reduce speed for the electric motor, changing a relative position between the body attachment 10 and the link for upper leg 22L (22R). In other words, the hip joint actuator 41L (41R) serves as an actuator, which applies rotational torque to the hip joint unit 21L (21R) to drive it. A base portion of the hip joint actuator 41L (41R) is secured to the actuator mounting member 13L (13R). An output shaft of the hip joint actuator 41L (41R) is secured to an upper distal portion of the link for upper leg 22L (22R), which corresponds to the location of the hip joint unit 21L (21R). In this way, the hip joint actuator 41L (41R) according to this embodiment is mechanically integrated with the hip joint unit 21L (21R). Rotation of the output shaft of the hip joint actuator 41L (41R) about Y-axis makes the link for upper leg 22L (22R) rotate about Y-axis relative to the body attachment 10 while the hip joint unit 21L (21R) acts as an axis for rotation. This allows the hip joint actuator 41L (41R) to produce torque between the body attachment 10 and the link for upper leg 22L (22R). When the hip joint actuator 41L (41R) does not produce torque, rotational resistance in the hip joint unit 21L (21R) decreases small enough to allow it free rotation, which prevents obstructing swing of a lower limb of the user P. Relationship between the hip joint actuator 41L (41R) and other components in terms of geometrical arrangement is not limited to what is described above. It may be alternatively possible that the hip joint actuator 41L (41R) is separate from the hip joint unit 21L (21R) and a drive unit for the hip joint unit 21L (21R) is added. In this arrangement the drive unit transfers a drive force generated by the hip joint actuator 41L (41R) to the hip joint unit 21L (21R).

The hip joint actuators 41L and 41R have encoders (rotary encoders) 81L and 81R, respectively. These encoders 81L and 81R are an example of "behavior detector" in the appended claims. The encoder 81L (81R) detects a rotational angle of the hip joint actuator 41L (41R) as data representative of behavior of the link for the lower limb 20L (20R). The resulting angle is sent to the controller 60.

The knee joint actuator 42L (42R) is mechanically integrated with and positioned coaxially with the hip joint actuator 41L (42R). The knee joint actuator 42L (42R) has an electric motor and reduction gears, which reduce speed of the electric motor, changing a relative position between the link for upper leg 22L (22R) and the link for lower leg 24L (24R). In this way, the knee joint actuator 42L (42R) serves as an actuator for applying rotational torque to the knee joint unit 23L (23R) so as to drive it. A base portion of the knee joint actuator 42L (42R) is secured to the actuator mounting member 13L (13R). An output shaft of the knee joint actuator 42L (42R) is secured to a distal portion of the first link 51L (51R). In this connection, relationship between the knee joint actuator 42L (42R) and other components in terms of geometrical arrangement is not limited to what is described above.

The knee joint actuators 42L and 42R have encoders (rotary encoders) 82L and 82R, respectively. These encoders 82L and 82R are an example of "behavior detector" in the appended claims. The encoder 82L (82R) detects a rotational angle of the knee joint actuator 42L (42R) as data representative of behavior of the link for the lower limb 20L (20R). The resulting angle is sent to the controller 60.

e. Drive Units 50L and 50R

As shown in FIGS. 1 to 4 and FIG. 7, the drive unit 50L (50R) (link for driving a knee joint unit) transfers a drive force generated by the knee joint actuator 42L (42R) to the knee joint unit 23L (23R). The drive unit 50L (50R) has a first link 51L (51R), a first joint unit 52L (52R), a second link 53L (53R) and a second joint unit 54L (54R).

One distal portion of the first link 51L (51R) is coupled with the output shaft of the knee joint actuator 42L (42R), and the other distal portion thereof is coupled with the first joint unit 52L (52R).

The first joint unit 52L (52R) couples the first link 51L (51R) and the second link 53L (53R) rotatably about Y-axis.

One distal portion of the second link 53L (53R) is coupled with the first joint unit 52L (52R), and the other distal portion thereof is coupled with the second joint unit 54L (54R).

The second joint unit 54L (54R) couples the second link 53L (53R) and the link for lower leg 24L (24R) rotatably about Y-axis.

Figure 3:
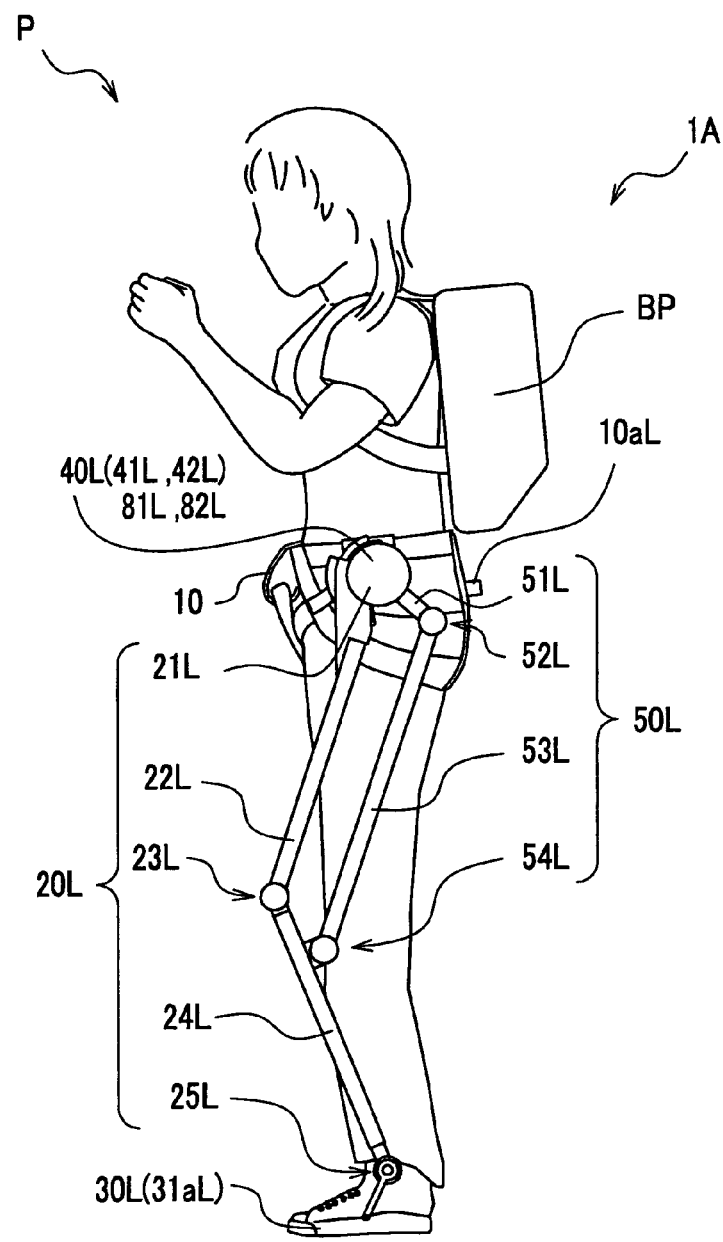
FIG. 3 is a side view illustrating an apparatus for assisting limb according to the present invention.

In this embodiment, the drive unit 50L (50R) is disposed behind the link for lower limb 20L (20R). Axial centers of the actuator unit 40L (40R), the knee joint unit 23L (23R), the second joint unit 54L (54R) and the first joint unit 52L (52R) are arranged so that they are located at corner points of a parallelogram. In other words, the link for upper leg 22L (22R), the first link 51L (51R), the second link 53L (53R) and a portion of the link for lower leg 24L (24R), which extends from the knee joint unit 23L (23R) to the second joint unit 54L (54R), make an approximate parallelogram. The apparatus 1A for assisting limb works while this geometrical relationship is maintained. This leads to easier detection, control and adjustment for an angle of a joint unit, allowing easier design of the apparatus 1A. An example of this is described as follows. Because a line segment defined by the knee joint unit 23L and the second joint unit 54L is always parallel with the first link 51L, as shown in FIG. 3, the controller 60 (see FIG. 11) is able to easily know geometrical relationship between the knee joint unit 23L and the second joint unit 54L, namely an angle made by the link for upper leg 22L and the link for lower leg 24L, based on an output from the encoder 82L.

Arrangement of the drive unit 50L (50R) and lengths of the links 51L (51R) and 53L (53R) are not limited to what are shown in the figures described above.

The present invention has the following features. A knee joint actuator having relatively large weight is not positioned near a knee of a user P but at a trunk of body (hip in this embodiment). A knee joint unit is driven by a drive force generated by the knee joint actuator, which is transferred by a drive unit. Also links and joint units, which are positioned alongside with a lower limb, are mechanically simplified.

In the present invention, the knee joint unit operates receiving a drive force generated by the knee joint actuator, which is transferred by a mechanism including a body attachment, links for upper leg, links for lower leg and drive units. In this way, it is possible to drive the knee joint unit with a low inertial moment.

f. Back Pack BP

The back pack BP, which is carried by a user P on his back, contains the controller 60 (see FIG. 11), an input/output interface 70 (see FIG. 11) and a battery (not shown). Description in detail will be given of the controller 60.

The input/output interface 70 provides an interface when an external computer is connected to the controller 60, for example. It may be possible to provide the controller 60 with personal data of the user P such as his weight via the external computer.

The battery supplies power to the load sensors 10$a$L and 10$a$R, the hip joint actuators 41L and 41R, the knee joint actuators 42L and 42R, the encoders 81L, 81R, 82L and 82R, the landing sensors 31$a$L and 31$a$R and the controller 60, respectively. The controller 60 controls supply of power generated by the battery.

In this connection, the back pack BP and the input/output interface 70 are not mandatory elements for the present invention. How the controller 60, the input/output interface 70 and the battery are attached to the user P is not limited to the method with the back pack BP described above. It may be alternatively possible to attach them directly to the body attachment 10.

g. Example of Operation

Description is given of an example of operation of the apparatus 1A for assisting limb according to the first embodiment. In FIGS. 8 and 9, only components of the apparatus 1A are schematically depicted, which are necessary for explanation.

Figure 8A:
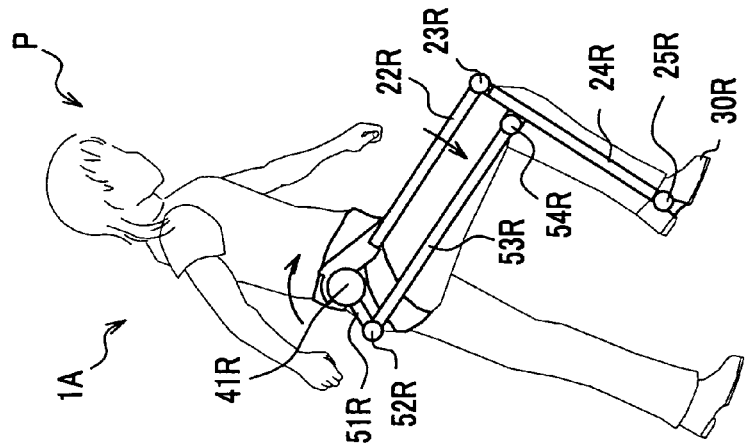
FIGS. 8A to 8C are each a schematic diagram illustrating movement of an apparatus for assisting limb.
Figure 8B:
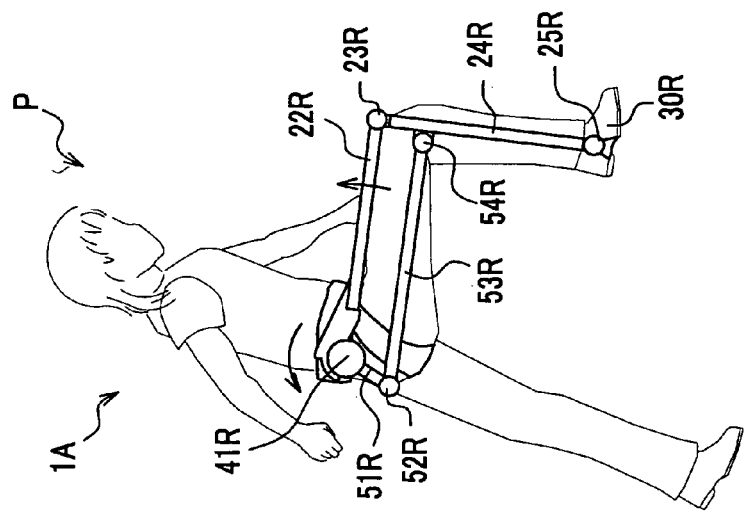

As shown in FIG. 8, the apparatus 1A for assisting limb drives the hip joint actuator 41R so as to rotate the link for upper leg 22R in a counter-clockwise direction, allowing an upper leg of a user P to move in a counter-clockwise direction (FIG. 8A to FIG. 8B).

Figure 8C:
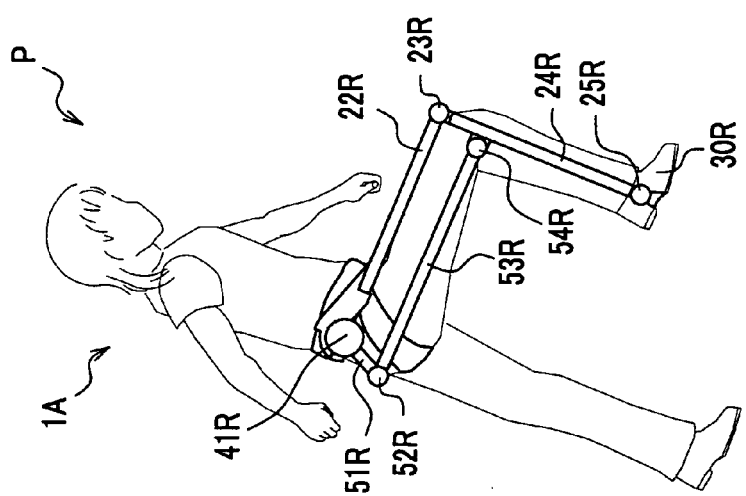

Similarly, the apparatus 1A drives the hip joint actuator 41R so as to rotate the link for upper leg 22R in a clockwise direction, allowing the upper leg of the user P to move in a clockwise direction (FIG. 8A to FIG. 8C).

As shown in FIG. 9, the apparatus 1A drives the knee joint actuator 42R so as to rotate the first link 51R in a counter-clockwise direction, which renders the second link 53R to depress the link for lower leg 24R via the second joint 54, so that the apparatus 1A is able to move a lower leg of the user P in a counter-clockwise direction (FIG. 9A to FIG. 9B).

Similarly, the apparatus 1A drives the knee joint actuator 42R so as to rotate the first link 51R in a clockwise direction, which renders the second link 53R to pull the link for lower leg 24R via the second joint 54R, so that the apparatus 1A is able to move the lower leg of the user P in a clockwise direction (FIG. 9A to FIG. 9C).

Although not shown, the similar description is applicable to a left lower limb of the apparatus 1A.

The apparatus 1A, which combines operations described above, is able not only to assist movement of a limb (lower limb), but also to support a part of weight of a user P by applying an assist force freeing the user P from his weight while the user P is walking.

h. Comparison of Inertial Moment

Description is given of a comparison in inertial moment between the apparatus 1A for assisting limb and a conventional apparatus.

FIG. 10A is a schematic diagram illustrating inertial moment in an apparatus according to the first embodiment. FIG. 10B is a schematic diagram illustrating inertial moment in a conventional apparatus. In FIG. 10B, a symbol representing an item of the conventional apparatus, which is a counterpart item of the apparatus 1A according to the first embodiment, is identified with a superscript "c".

As shown in FIG. 10A, when a user P wearing the apparatus 1A walks, inertial moment about an axis of hip joint of the user P (Y-axis) occurs due to the self weight of the apparatus 1A.

Weight of each member, its center of gravity and distance from the axis of hip joint are defined as follows:

m1: weight of a hip joint actuator 41R
r1: distance between a hip joint actuator 41R and an axis of hip joint (=0)
m2: weight of a knee joint actuator 42R
r2: distance between a knee joint actuator 42R and an axis of hip joint (=0)
m3: weight of a link for upper leg 22R
r3: distance between the center of gravity of a link for upper leg 22R and an axis of hip joint
m4: weight of a link for lower leg 24R
r4: distance between the center of gravity of a link for lower leg 24R and an axis of hip joint
m5: weight of a foot attachment 30R
r5: distance between the center of gravity of a foot attachment 30R and an axis of hip joint
m6: weight of a drive unit 50R
r6: distance between the center of gravity of a drive unit 50R and an axis of hip joint With the definition described above, an inertial moment Ih due to components, which form a right lower limb unit of the apparatus 1A, about the axis of hip joint is approximated by the following expression.

$$Ih = m3 \times r3^2 + m4 \times r4^2 + m5 \times r5^2 + m6 \times r6^2$$

As shown in FIG. 10B, when a user P walks wearing a conventional apparatus 1A$^c$ for assisting limb, an inertial moment about an axis of hip joint of the user P (Y-axis) occurs due to self weight of the apparatus 1A$^c$. This apparatus 1A$^c$ has a knee joint actuator 42R$^c$, between a link for upper leg 22R$^c$ and a link for lower leg 24R$^c$, eliminating a drive unit.

Weight of each member, its center of gravity and distance from the axis of hip joint are defined as follows:

m11: weight of a hip joint actuator 41R$^c$ (=m1)
r11: distance between a hip joint actuator 41R$^c$ and an axis of hip joint (=r1=0)
m12: weight of a knee joint actuator 42R$^c$ (=m2)
r12: distance between the center of gravity of a knee joint actuator 42R$^c$ and an axis of hip joint
m13: weight of a link for upper leg 22R$^c$ (=m3)
r13: distance between the center of gravity of a link for upper leg 22R$^c$ and an axis of hip joint (=r3)
m14: weight of a link for lower leg 24R$^c$ (=m4)
r14: distance between the center of gravity of a link for lower leg 24R$^c$ and an axis of hip joint (=r4)
m15: weight of a foot attachment 30R$^c$ (=m5)
r15: distance between the center of gravity of a foot attachment 30R$^c$ and an axis of hip joint (=r5)

With the definition described above, an inertial moment Ih$^c$ due to components, which form a right lower limb unit of the apparatus 1A$^c$, about the axis of hip joint is approximated by the following expression.

$$Ih^c = m12 \times r12^2 + m3 \times r3^2 + m4 \times r4^2 + m5 \times r5^2$$

As the knee joint actuator 42R$^c$ is generally heavier than the drive unit 50R (m12>m6) and lies remoter from the axis of hip joint (r12>r6), 1h<1h$^c$ is satisfied. In this way, it is possible for the apparatus 1A for assisting limb to decrease the inertial moment due to movement of the user P so as to reduce a load imposed on the user P. This leads to improvement in feeling of a user wearing the apparatus 1A, which restrains fatigue from developing in the user. Because the knee joint actuator 42L (42R) having relatively large weight is positioned integrally with the hip joint actuator 41L (41R), it is possible to decrease a load (inertial moment) imposed on the hip joint actuator 41L (41R), which results in miniaturization and power reduction for the hip joint actuator 41L (41R).

Description in detail is given of the controller 60.

Figure 11:
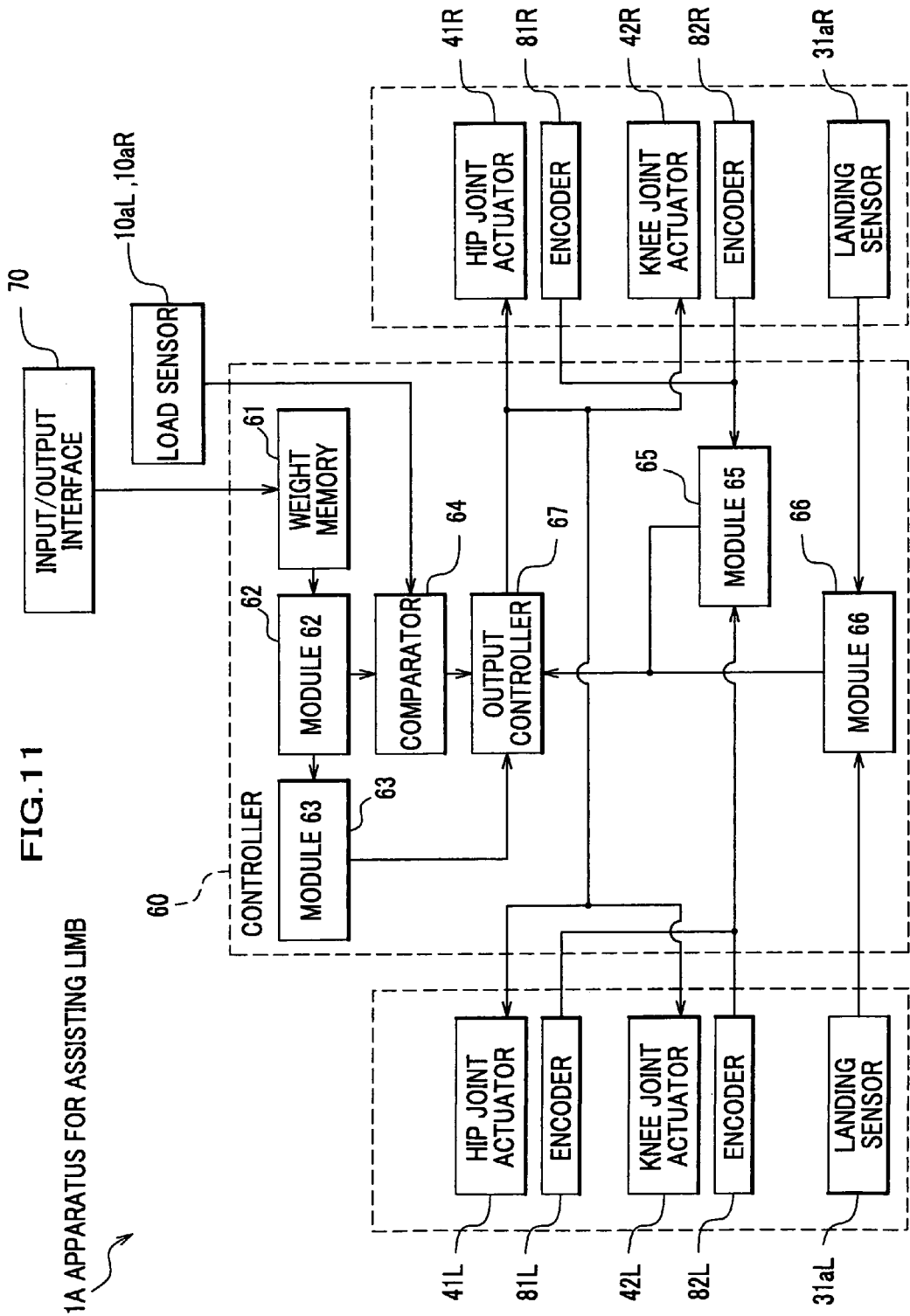
FIG. 11 is a functional block diagram showing an apparatus for assisting limb according to the present invention.

As shown in FIG. 11, the controller 60 includes a weight memory 61, a module 62 for calculating target assist force, a module 63 for calculating initial torque, a comparator 64, a module 65 for detecting actuator state, a module 66 for determining landed foot and an output controller 67.

The weight memory 61 acquires weight (weight data) of the user P and stores (temporarily stores) it. It may be possible that the user P enters his weight into the controller 60, or the controller 60, which recognizes the user P, reads out weight of the user P from the weight memory 61, which stores weight data in advance. It may be alternatively possible for an external computer to enter weight of the user P into the weight memory 61 via the input/output interface 70. Furthermore, it may be alternatively possible for the weight memory 61 to store single weight of a user P.

The module 62 for calculating target assist force reads out weight data stored in the weight memory 61, calculating a target assist force based on the weight data.

The target assist force is a target value for the force applied to the user P by the apparatus 1A for assisting limb, which is directed in Z-direction when the user P vertically stands on a horizontal floor. A given percentage of the weight of the user P, 30% for example, is selected as the target value. In this embodiment, a minimum assist force Fa1 and a maximum assist fore Fa2 in addition to a target assist force Fa are calculated. The minimum assist force Fa1 and maximum assist force Fa2 correspond to "lower limit" and "upper limit" shown in the appended claims, respectively.

When 30% of weight is selected as a target assist force Fa, a minimum assist force Fa1 of 28% and a maximum assist force Fa2 of 32% are generated, for example. These assist forces Fa, Fa1 and Fa2 are selected appropriately according to a desirable assist force applied to the user P, calculation capacity of the controller 60, characteristics of the actuators 41L, 41R, 42L and 42R and characteristics of sensors 10aL, 10aR, 31aL and 31aR.

It may be possible to adjust the target assist force Fa, the minimum assist fore Fa1 and the maximum assist force Fa2; for example, adopting arbitrary values with an external computer via the input/output interface 70.

The module 63 for calculating initial torque calculates initial torque to be applied to each of the hip joint actuators 41L and 41R and the knee joint actuators 42L and 42R based on a target assist force Fa.

This initial torque is calculated for each of three cases such as (1) a both-foot landed phase, (2) a left-foot landed phase (right-foot lifted phase) and (3) a right-foot landed phase (left-foot lifted phase).

For a both-foot landed phase (1), initial torque applied to each of the hip joint actuators 41L and 41R and the knee joint actuators 42L and 42R is calculated.

For a left-foot landed case (2), initial torque applied to each of the hip joint actuator 41L and the knee joint actuator 42L is calculated. In this case, initial torque applied to each of the hip joint actuator 41R and the knee joint actuator 42R is equal to zero.

For a right-foot landed case (3), initial torque applied to each of the hip joint actuator 41R and the knee joint actuator 42R is calculated. In this case, initial torque applied to each of the hip joint actuator 41L and the knee joint actuator 42L is equal to zero.

The initial torque described above is intended to improve an initial response for the apparatus 1A for assisting limb. It may be preferable, but not necessarily, that the initial torque is so adjusted that the apparatus 1A smoothly and promptly transfers from an initial state to a state of providing target assist force Fa. Because torque is applied to each actuator in an initial state according to initial torque, the apparatus 1A is able to prevent the user P from falling and losing balance so as to help the user P to keep stable standing posture, even if the user P suddenly puts his weight on the apparatus 1A. The initial state includes a moment when the apparatus 1A is started up, a moment when the apparatus 1A changes landing phases (a both-foot landed phase to a foot landed phase, a foot landed phase to a both-foot landed phase).

Applying initial torque also contributes to prevention of failure of the apparatus 1A.

As torques required for the actuators 41L, 41R, 42L and 42R vary according to assist forces Fa, Fa1 and Fa2 and rotational angles of the actuators 41L, 41R, 42L and 42R, it may be alternatively possible to determine an initial torque, taking into account a current rotational angle of each actuator in addition.

The comparator 64 compares a current assist force Fb (hereinafter simply referred to as "load Fb") based on weight detected by the load sensors 10aL and 10aR and an output calculated by the module 62 for calculating target assist force. The comparator 64 stores a relationship between an actual value detected by the load sensor 10aL (10aR) and an assist force, which is applied by the link for lower limb 20L (20R) based on the actual value. In this way, the comparator 64 is able to acquire an actually acting assist force based on the output delivered by the load sensor 10aL (10aR).

There are three types of cases resulting from comparison: Fb<Fa1, Fa1≦Fb≦Fa2 and Fb>Fa2.

These results are sent to the output controller 67.

The module 65 for detecting actuator state detects a state for each joint unit based on outputs from the hip joint encoders 81L and 81R and the knee joint encoders 82L and 82R. Results are sent to the output controller 67.

The module 66 for determining landed foot determines which phase, (1) a both-foot landed phase, (2) a left-foot landed phase or (3) a right-foot landed phase, is occurring based on outputs from the landing sensors 31aL and 31aR.

If there is output from both landing sensors 31aL and 31aR, the module 66 determines that a both-foot landed phase is occurring.

If there is output from only the landing sensor 31aL, the module 66 determines that a left-foot landed phase (right-foot lifted phase) is occurring.

If there is output from only the landing sensor 31aR, the module 66 determines that a right-foot landed phase (left-foot lifted phase) is occurring.

The resulting determination is sent to the output controller 67.

The output controller 67 determines an output for each of the actuators 41L, 41R, 42L and 41R based on calculation results from the module 63, comparison results from the comparator 64, detection results from the module 65 and determination results from the module 66, instructing each actuator to generate the output.

The output controller 67 predicts behavior of the links for lower limb 20L and 20R based on detection results from the module 65 and their differentials, determining an output for each of the actuators 41L, 41R, 42L and 42R based on the prediction.

Figure 17A:
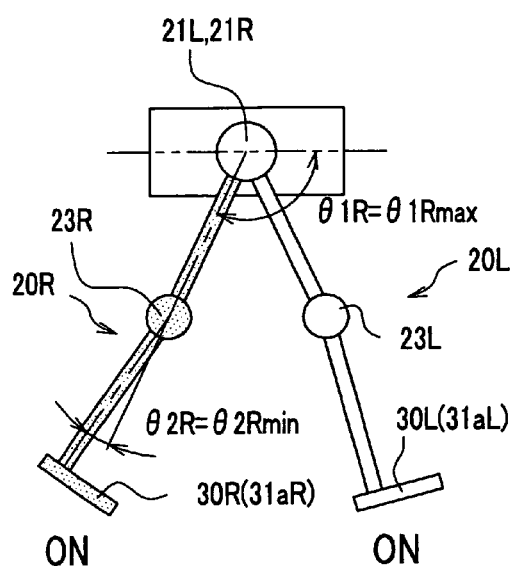
FIGS. 17A to 17D are each a schematic diagram illustrating transition of state for a link for right lower limb while a user is walking.

When an angle θ1R increases to reach a predetermined value, which is, for example, set as an angle at which a right-foot was lifted from a floor at a previous time, as shown in FIG. 17A, it is expected that the right foot is soon leaving away from the floor. The controller 60 acquires to store an angle θ1L (θ1R) of a previous movement at a time of a foot leaving away from the floor based on output from the landing sensor 31*a*L (31*a*R) and the encoder 81L (81R). The angle θ1L (θ1R) is called a floor leaving angle, which corresponds to a rotational angle of the hip joint actuator 41L (41R). The controller 60 predicts behavior of a leg of the user P according to the floor leaving angel θ1.

By shifting allocation of an assist force to the left link for lower limb 20L, it is possible for the apparatus 1A to prepare for a transition, in which a right foot of the user P is in a lifted phase and only a left system (the body attachment 10, the link for lower limb 20L and the foot attachment 30L) is required to support weight of the user P. This contributes to smooth variation of torque output generated by an actuator at a time of shifting. In this way, it is possible to implement more stable assist for freeing the user P from weight.

i. Direction of Torque Generation

Description is given of directions of torque generated by the hip joint actuators 41L and 41R and the knee joint actuators 42L and 42R. In the drawings described below, "ON" is meant to represent that the foot attachments 30L and 30R are landed on a floor. "OFF" is meant to represent otherwise.

As shown in FIG. 12, a straight line L1 runs horizontally alongside with the waist belt 11. A straight line L2 extends in a longitudinal direction of the links for upper leg 22L and 22R. An angle θ1L (θ1R) is made by the straight line L1 and the link for upper leg 22L (22R). Similarly, an angle θ2L (θ2R) is made by the straight line L2 and the link for lower leg 24L (24R).

When the apparatus 1A for assisting limb provides a sufficient assist force, as shown in FIG. 12A, the user P is able to keep standing posture without supporting all weight by his lower limb.

When the user P lacks capacity of lower limb enough to support his weight and the apparatus 1A does not provide a sufficient assist force, the apparatus 1A changes posture of the user P in such a manner that the angles θ1L and θ1R decrease but the angles θ2L and θ2R increase.

In view of the above discussion, the problem can be resolved if the hip joint actuators 41L and 41R (see FIG. 1) generate torque so that the angles θ1L and θ1R increase, and in contrast, the knee joint actuators 42L and 42R generates torque so that the angles θ2L and θ2R decreases.

Each of the actuators 41L, 41R, 42L and 42R is controlled so that a moving range for each of the joint units 21L, 21R, 22L and 22R does not exceed that for a joint of an ordinary person, which contributes to safety of a user. The length of the link for upper leg 22L (22R), the knee joint unit 23L (23R) and the link for lower leg 24L (24R) is so adjusted that the link for upper leg 22L (22R) and the link for lower leg 24L (24R) are not aligned so straight as a line even if the user P is in standing posture. Accordingly, the knee joint unit 23L (23R) is kept so as not to be in a straightened position. In other words, it is adjusted that the link for upper leg 22L (22R) and the link for lower leg 24L (24R) neither form a straight line nor make a reversely bent angle. The configuration described above is shown in FIGS. 3 and 4, which is intended to avoid not only a singular point at which the link for upper leg 22L (22R) and the leg for lower leg 24L (24R) are aligned in a straight line, but also a reverse angle which occurs when these links move further than the straightened position. In this way, it is possible to relax an impact force imposed on the body attachment 10 and the foot attachments 30L and 30R of the user P and increase control capacity for an assist force implemented by the actuators 41L, 41R, 42L and 42R. It may be alternatively possible to add a mechanical stopper to each of the actuators 41L, 41R, 42L and 42R and the links 22L, 22R, 24L and 24R so as to reliably limit a motion range.

j. Relation Between Generated Torque and Assist Force

Description is given of relationship between torque generated by an actuator and an assist force.

Figure 13:
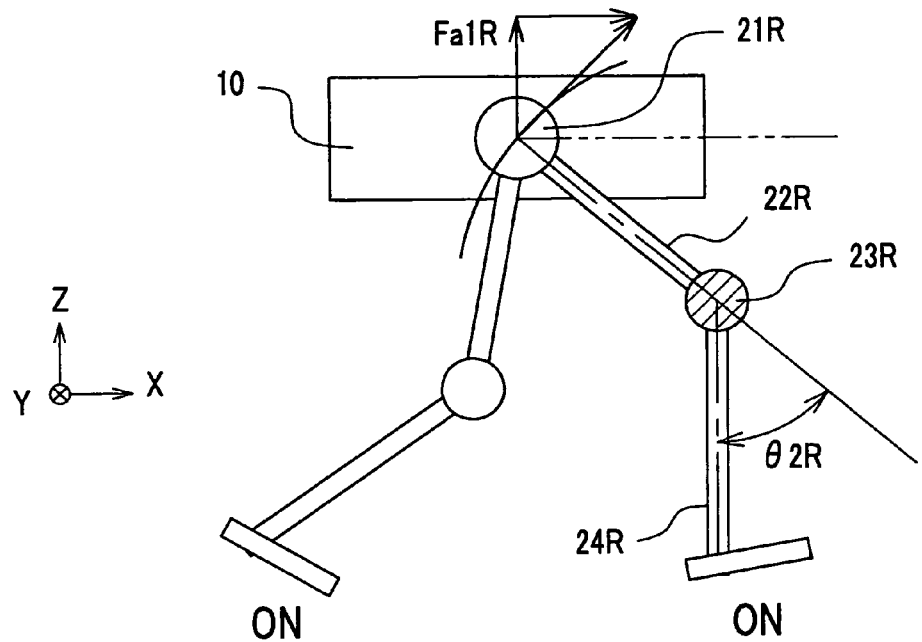
FIG. 13 is a schematic diagram illustrating relationship between torque generated by a knee joint actuator and an assist force.

Description is first given of relationship between torque generated by the knee joint actuator 42R and an assist force with reference to FIG. 13. It is assumed that the hip joint actuator 41R is fixed so as not to rotate.

When the foot attachment 30R is landed and the knee joint actuator 42R generates torque so that the angle θ2R decreases, a rotational force is applied to the hip joint actuator 41R in a tangential direction with respect to a circle whose center lies in the knee joint actuator 42R. A component of this rotational force in an antigravitational direction (Z-axis component) results in an assist force Fa1R applied by the knee joint actuator 42R.

Figure 14:
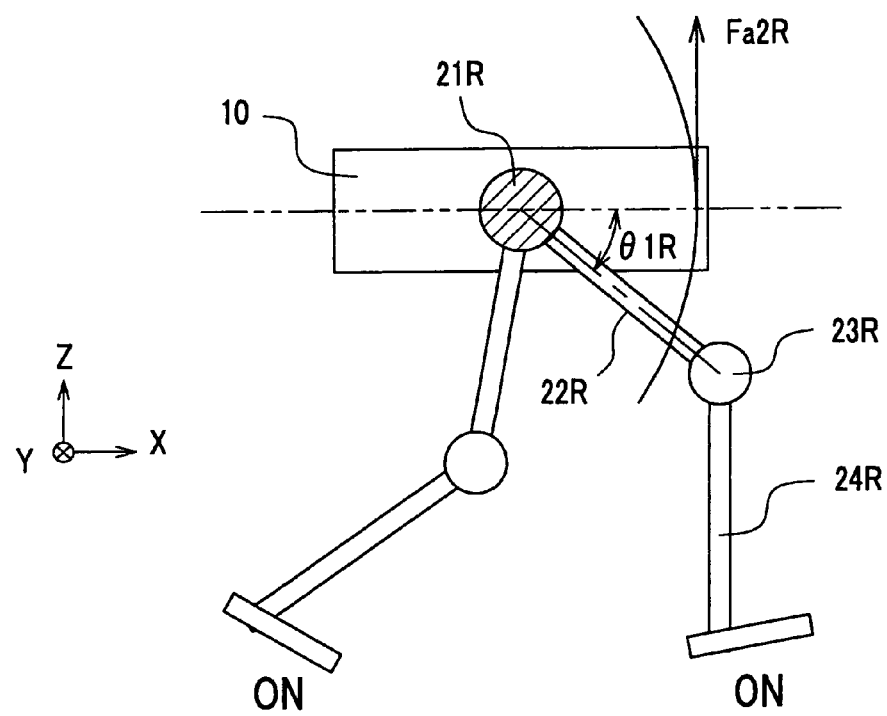
FIG. 14 is a schematic diagram illustrating relationship between torque generated by a hip joint actuator and an assist force.

Description is given of relationship between torque generated by the hip joint actuator 41R and an assist force with reference to FIG. 14. It is assumed that the knee joint actuator 42R is fixed so as not to rotate.

When the foot attachment 30R is landed and the hip joint actuator 41R generates torque so that the angle θ1R increases, a rotational force is applied to the body attachment 10 in a tangential direction with respect to a circle whose center lies in the hip joint actuator 41R. A component of this rotational force in an antigravitational direction (Z-axis component) results in an assist force Fa2R applied by the hip joint actuator 41R.

Though not shown graphically, an assist force Fa1L generated by the knee joint actuator 42L and an assist force Fa2L by the hip joint actuator 41L are generated appropriately, and an assist fore (total assist force) Fa applied by the apparatus 1A for assisting limb is represented by the following expressions.

$$Fa = Fa1R + Fa2R + Fa1L + Fa2L \quad (1) \text{ Both-foot landed phase}$$

$$Fa = Fa1L + Fa2L \quad (2) \text{ Left-foot landed phase}$$

$$Fa = Fa1R + Fa2R \quad (3) \text{ Right-foot landed phase}$$

k. Load of Foot Attachment

Figure 15:
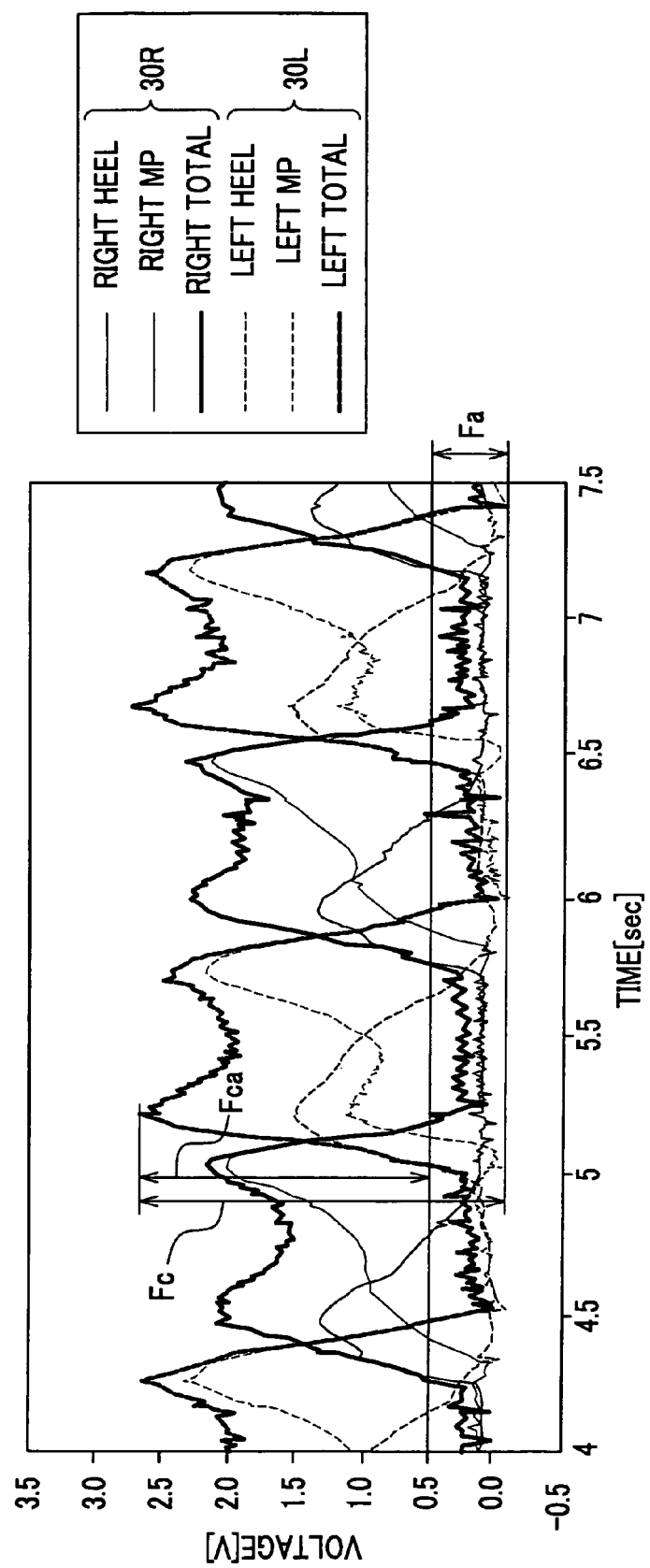
FIG. 15 is a graph showing results of measured pressure imposed on a foot attachment.

Description is given of a load imposed on the foot attachments 30L and 30R. FIG. 15 describes a shift of pressure and an effect resulting from the apparatus 1A for assisting limb.

A user P demonstrated walking who wore the apparatus 1A when two pressure sensors were attached to two locations of a rear side of the foot attachment 30L (30R), a heel and a metatarsal joint (MP). Output of the sensors is shown in the form of voltage. From these graphs, it is known that a load is alternately imposed on the foot attachments 30L and 30R, shifting from a heel to a toe. The apparatus 1A applies an assist force Fa to the user P, decreasing a maximum load imposed on a foot of the user P (Fc→Fca) so as to provide easier walking.

l. Example of Operation of an Apparatus for Assisting Limb

Description is given of operation of an apparatus 1A for assisting limb.

Weight of a user P is entered into a controller 60 while he wears an apparatus 1A for assisting limb. The weight is stored in a weight memory 61 (step S1).

A module 62 for calculating target assist force calculates a target assist force Fa (Fa1, Fa2) based on the weight of the user P stored in the weight memory 61 (step S2).

A module 63 for calculating initial torque calculates initial torque based on the target assist force Fa (step S3).

A module 66 for determining landed foot specifies a landed foot based on output from landing sensors 31*a*L and 31*a*R (step S4).

When the module 66 determines that only a left foot is landed, an output controller 67 drives a hip joint actuator 41L and a knee joint actuator 42L so as to generate torque according to the initial torque (step S5a).

When the module 66 determines that both feet are landed, the output controller 67 drives hip joint actuators 41L and 41R as well as knee joint actuators 42L and 42R so as to generate torque according to the initial torque (step S5b).

When the module 66 determines that only a right foot is landed, the output controller 67 drives a hip joint actuator 41R and a knee joint actuator 42R so as to generate torque according to initial torque (step S5c).

Load sensors 10aL and 10aR detect a load Fb (step S6). A comparator 64 compares the detected load Fb and the calculated target assist force Fa (Fa1, Fa2) (step S7).

When the load (current assist force) Fb is less than the target assist force Fa1, the output controller 67 increases current supplied to an actuator on a side of a landed foot by a predetermined amount so as to increase output torque by a given amount (step S8a).

When Fb lies between Fa1 and Fa2 both inclusive, the output controller 67 keeps torque constant, which is generated by the actuator on a side of a landed foot (step S8b).

When Fb is greater than Fa2, the output controller 67 decreases current supplied to an actuator on a side of a landed foot by a predetermined amount so as to decrease output torque by a given amount (step S8c).

In this connection, it may be possible to appropriately select the predetermined amounts for increasing and decreasing the current, respectively, according to calculation capacity of the controller 60, characteristics of the actuators 41L, 41R, 42L and 42R and the sensors 10aL, 10aR, 31aL and 31aR.

When an OFF signal is entered into the controller 60 (Yes in step S9), the apparatus 1A terminates processing. When an OFF signal is not entered into the controller 60 (No in step S9), the module 66 determines whether or not there has been a change of landed foot (step S10).

When there is a change, a both-foot landed phase→a foot landed phase, a foot landed phase→a both-foot landed phase, (Yes in step S10), the flow returns to step S4. In contrast, when there is no change (No in step S10), the flow returns to step S6.

m. State Transition of Link for Lower Limb and Torque Generation

Description is given of a state transition of an apparatus 1A for assisting limb in response to walking of a user P, paying attention to a state transition of a right link for lower limb 20R.

It should be noted that FIGS. 17A, 17B, 17C, 17D, 18A, 18B and 18C each show a typical example, and a manner of walking and an angle of knee during waking differ from user to user.

When a right lower limb of the user P lies in an extreme backward position (FIG. 17A; state 1), a link for upper leg 22R and a link for lower leg 24R come close to an aligned position like a straight line. At this moment, an angle $\theta 1R$ has a maximum value ($\theta 1R=\theta 1Rmax$) but an angle $\theta 2R$ has a minimum value ($\theta 2R=\theta 2Rmin$). Because a right foot attachment 30R is landed, a hip joint actuator 41R generates torque so as to increase the angle $\theta 1R$. In contrast, a knee joint actuator 42R generates torque so as to decrease the angle $\theta 2R$.

Figure 17B:
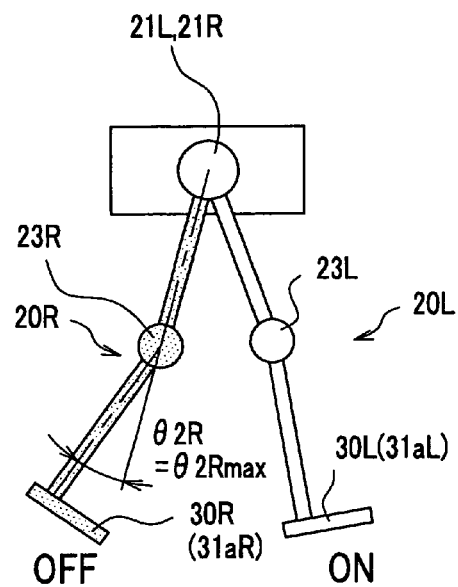

When the user P swings out his right lower limb (in X-axis direction), his right foot (foot attachment 30R) is lifted from a floor. Output torque generated by the hip joint actuator 41R and the knee joint actuator 42R will be zero. Because the angle $\theta 1R$ progressively decreases and the foot attachment 30 follows with delay relative to a knee joint unit 23R after lifting of the right foot from the floor, the angle $\theta 2R$ increases for a while. When the angle $\theta 2R$ takes a maximum value ($\theta 2R=\theta 2Rmax$), the knee joint unit 23R start swinging forward (FIG. 17B; state 2).

Figure 17C:
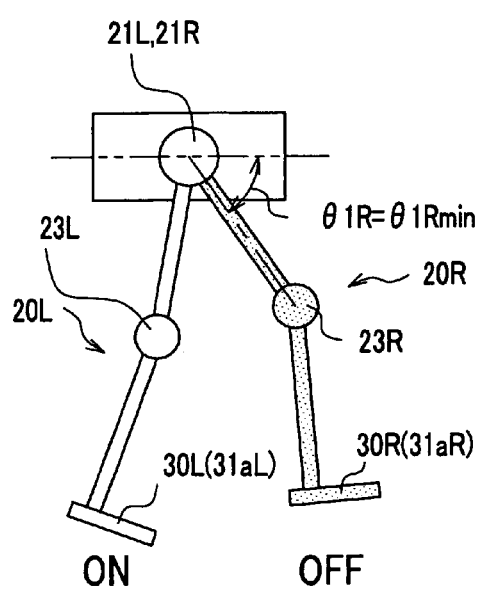
Figure 17D:
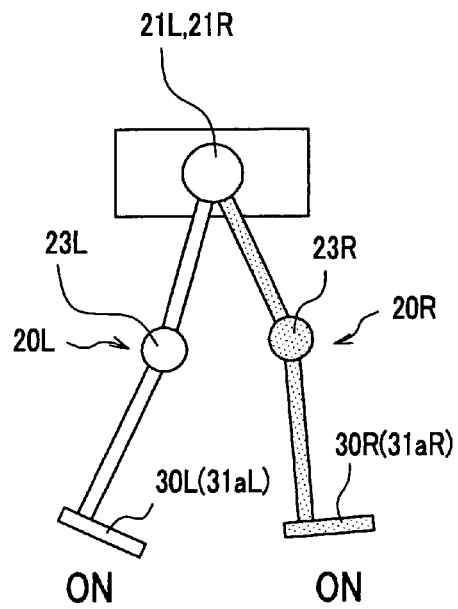
Figure 18A:
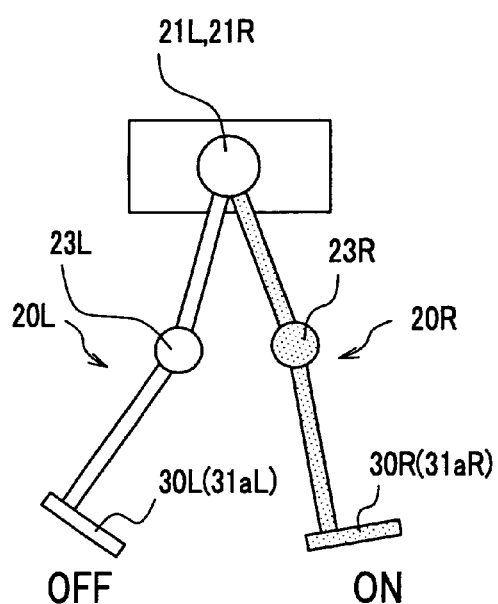
FIGS. 18A to 18C are each a schematic diagram illustrating transition of state for a link for right lower limb while a user is walking.
Figure 18B:
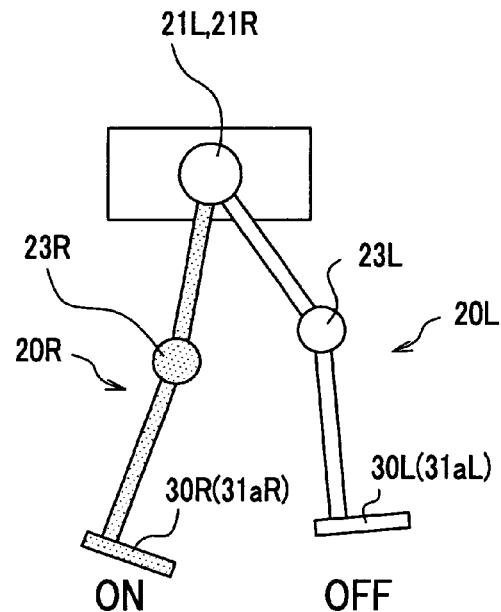
Figure 18C:
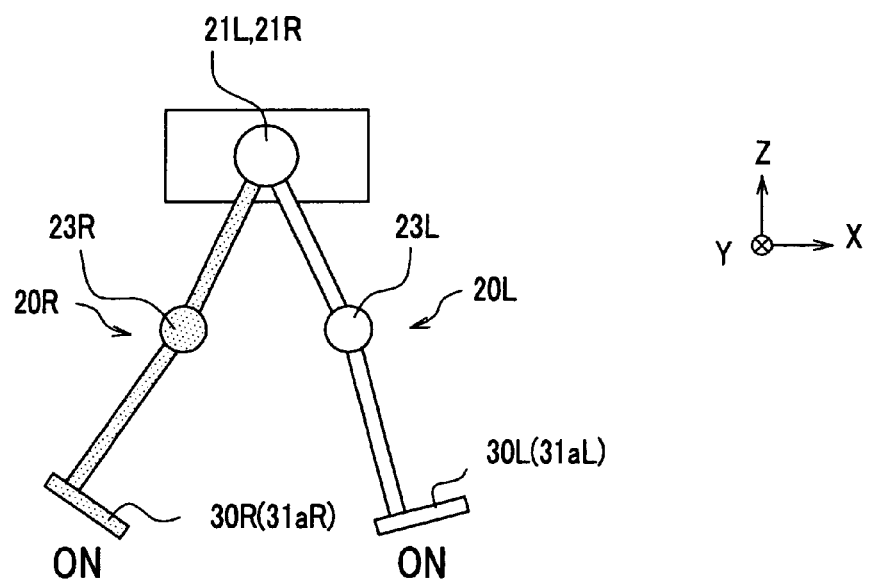

If the user P continues to swing his right lower limb forward after the state 2, the angle $\theta 1R$ takes a minimum value ($\theta 1R=\theta 1Rmin$) (FIG. 17C; state 3). Since the angle $\theta 1R$ progressively increases and the foot attachment 30R comes forward with delay relative to the knee joint unit 23R, the angle $\theta 2R$ progressively decreases. In this way, the right foot attachment 30R lands on the ground (FIG. 17; state 4). When a left lower limb of the user P moves in a similar manner as the right lower limb (FIG. 18A; state 5, FIG. 18B; state 6, FIG. 18C; state 7=state 1), namely a right foot lands on the ground, the hip joint actuator 41R continuously generates torque so as to increase the angle $\theta 1R$. In contrast, the knee joint actuator 42R continuously generates torque so as to decrease the angle $\theta 2R$.

In this connection, it may be alternatively possible for the hip joint actuator 41R to generate torque in a counter-clockwise direction in FIG. 17 when the foot is lifted so that an assist force is applied to an upper leg of the user, which helps the user P to swing forward the upper leg.

The apparatus 1A for assisting limb can provide the following advantages.

The apparatus 1A described above, in which an inertial moment due to motion of the user P is decreased and a load imposed on the user is relaxed, is able to increase feeling of the user wearing the apparatus 1A and prevent fatigue experienced by the user.

The apparatus 1A described above, which supports a part of weight of the user P, is able to reduce a load imposed on a lower limb of the user by his weight.

The apparatus 1A described above, which detects a load imposed on it and supports a predetermined percentage of the weight of the user P based on the detected load, is able to provide appropriate assistance to the user P according to a change in his posture.

The apparatus 1A described above, which applies an assist force only to a landed lower limb, is able not only to provide an appropriate assist force according to a change in walking posture, but also not to obstruct movement of a lifted lower limb.

The apparatus 1A described above does not require manipulation by a hand of the user, different from a stick, such as a crutch and a four-point stick. It is possible for the user P to use his hands freely during walking with the apparatus 1A. In addition, the apparatus 1A is free from possible fatigue for an arm and upper trunk of the user P while used long hours.

The apparatus 1A described above, which is compactly configured alongside with a lower limb of the user P, does not cause obstruction when the user P moves in a narrow passage, stairs and the like. Because the links 22L, 22R, 24L and 24R and the joint units 21L, 21R, 23L, 23R, 25L and 25R, which are designed to be similar to counterparts of a lower limb of a human, are placed alongside with a lower limb of the user P, the apparatus 1A tends to better collaborate with human walking so as to provide better efficiency in terms of assist force than a conventional apparatus, which uses a directly coupled actuator or which is attached more remotely from the lower limb.

The apparatus 1A described above, which does not employ wheels, is available irrespective of conditions of floor.

The apparatus 1A described above, which restricts the user P at a fewer locations, is suitable for long-hour use. Because the apparatus 1A, which does not require restriction for knees, upper legs and the like, is able to eliminate most restriction for a lower limb of the user P, he is freed from feeling uncomfortable restriction, pain and high load. The fewer restricting locations enable further weight reduction of the apparatus 1A. Because the apparatus 1A is so versatile that one typical type can be applied to different users without being affected by the shape and walking habit of a user P, it meets an all-purpose application.

Figure 4:
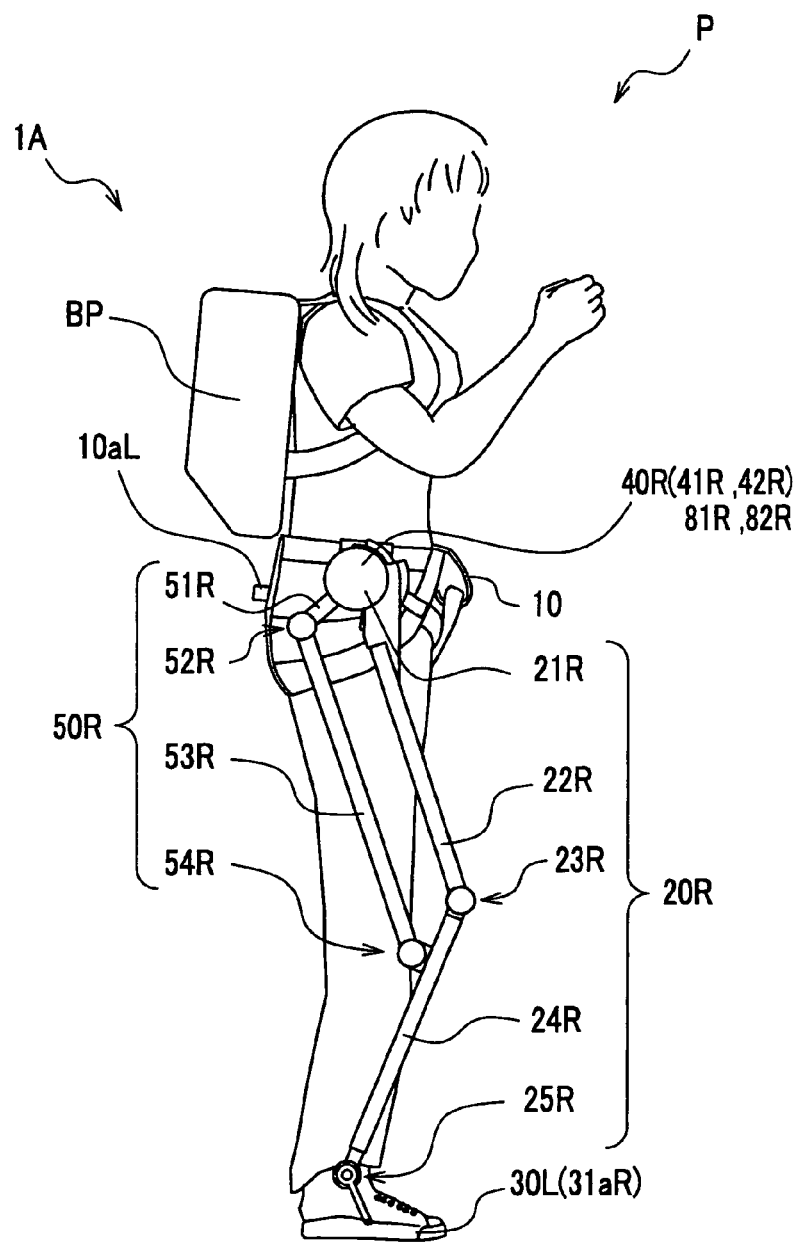
FIG. 4 is a side view illustrating an apparatus for assisting limb according to the present invention.

The apparatus 1A has a feature that a portion of the user P to which an assist force is applied by the apparatus 1A (mounting portions of the actuator units 40L and 40R) and where the user P put his weight both lie in the substantially same vertical plane (Y-Z plane in FIGS. 3 and 4). This arrangement prevents the apparatus 1A from giving unnecessary moment in a pitch direction (about Y-axis) to the user P while the apparatus 1A applies an assist force.

II. Second Embodiment

Figure 19:
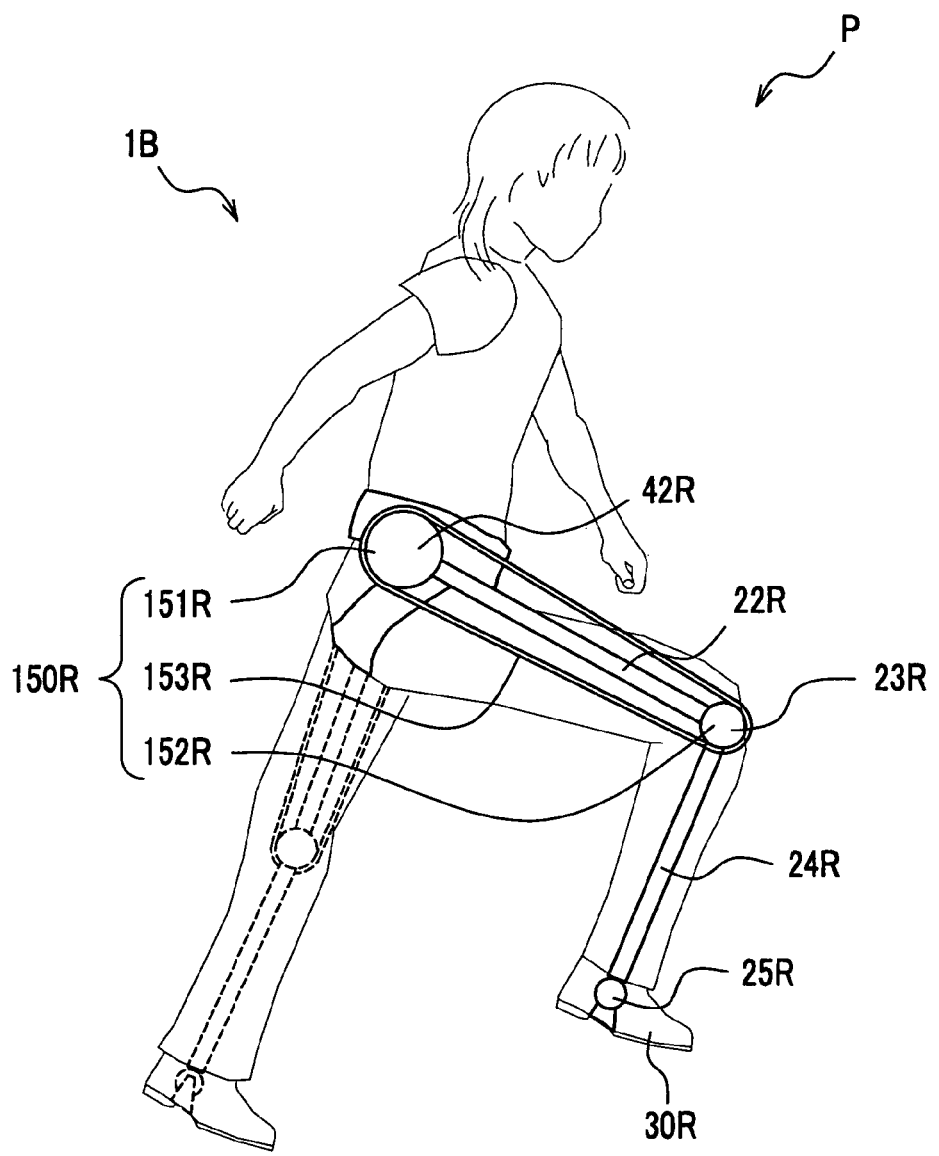
FIG. 19 is a side view illustrating an apparatus for assisting limb according to the present invention.
Figure 20:
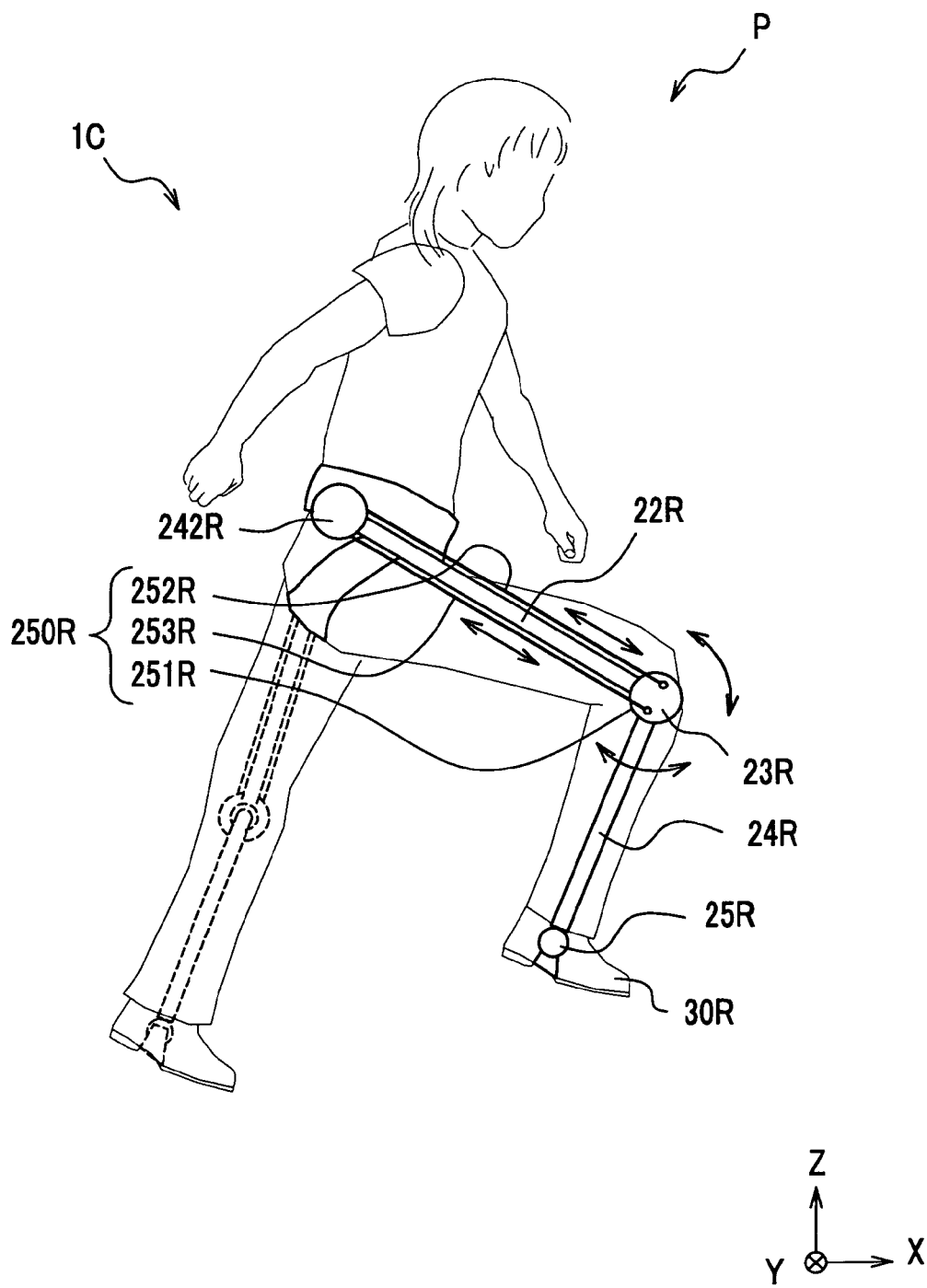
FIG. 20 is a side view illustrating an apparatus for assisting limb according to the present invention.
Figure 21:
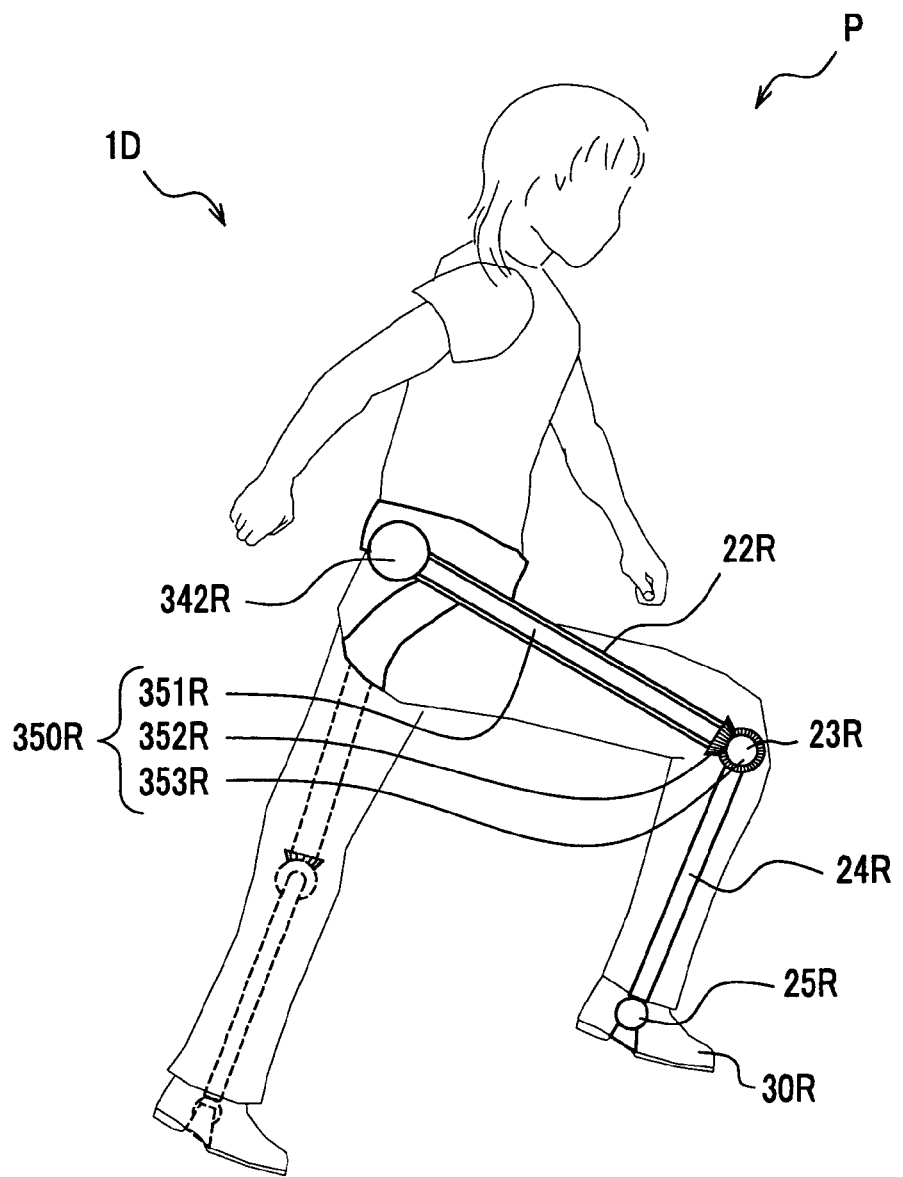
FIG. 21 is a side view illustrating an apparatus for assisting limb according to the present invention.

Description is given of an apparatus for assisting limb according to a second embodiment of the present invention, focusing on differences with respect to an apparatus 1A for assisting limb according to the first embodiment. In the following drawings which are referred to in description of embodiments, only relevant portions are schematically described, which are necessary for making a comparison with the apparatus 1A according to the first embodiment. In FIGS. 19-21, for example, a hip joint actuator 41R is omitted.

In FIGS. 19 to 22, because left and right components are identical in architecture, symbols are only given to the right components, omitting those for the left ones.

As shown in FIG. 19, an apparatus 1B for assisting limb according to the second embodiment of the present invention has a drive unit 150R instead of a drive unit 50R.

The drive unit 150R has a first pulley 151R, a second pulley 152R and an endless belt 153R. The first pulley 151R, which is coupled with a knee joint actuator 42R, rotates synchronously with its shaft. The second pulley 152R is attached to a link for lower leg 24R. The endless belt 153R turns around the first and second pulleys 151R and 152R.

The knee actuator 42R rotates the first pulley 151R, advancing or pulling back the endless belt 153R, which rotates the second pulley 152R. In this way, a knee joint 23R is driven.

III. Third Embodiment

Description is given of an apparatus for assisting limb according to a third embodiment of the present invention, focusing on differences with respect to an apparatus 1A for assisting limb according to the first embodiment.

As shown in FIG. 20, an apparatus 1C according to the third embodiment has not only a knee joint actuator 242R instead of a knee joint actuator 42R, but also a drive unit 250R instead of a drive unit 50R.

The drive unit 250R has a wire mounting member 251R, a knee joint actuator 242R and two wires 252R and 253R. The wire mounting member 251R, which is integrally coupled with a link for lower leg 24R, is located in an outer portion of a knee joint unit 23R. The two wires 252R and 253R are routed between the wire mounting member 251R and the knee joint actuator 242R.

The knee joint actuator 242R drives the knee joint unit 23R by pulling the wire 252R and loosening the wire 253R, or vice versa.

IV. Fourth Embodiment

Description is given of an apparatus for assisting limb according to a fourth embodiment of the present invention, focusing on differences with respect to an apparatus 1A for assisting limb according to the first embodiment.

As shown in FIG. 21, an apparatus 1D according to the fourth embodiment has not only a knee joint actuator 342R instead of a knee joint actuator 42R, but also a drive unit 350R instead of a drive unit 50R.

The drive unit 350R has a shaft 351R, a first bevel gear 352R and a second bevel gear 353R. The shaft 351R is coupled with an output shaft of the knee joint actuator 342R. The first bevel gear 352R is attached to a distal portion of the shaft 351R. The second bevel gear 353R, which is attached to a link for lower leg 24R, engages with the first bevel gear 352R.

The knee joint actuator 342R drives the shaft 351R about its axis, driving a knee joint unit 23R.

In this connection, it may be alternatively possible to adopt other types of gears, which transfer a drive force generated by a knee joint actuator to a knee joint unit so as to drive it. The gears include a helical gear, a straight bevel gear, a spiral bevel gear, a face gear, a hypoid gear, a worm gear and the like.

V. Fifth Embodiment

Description is given of an apparatus for assisting limb according to a fifth embodiment of the present invention, focusing on differences with respect to an apparatus 1A for assisting limb according to the first embodiment.

Figure 22:
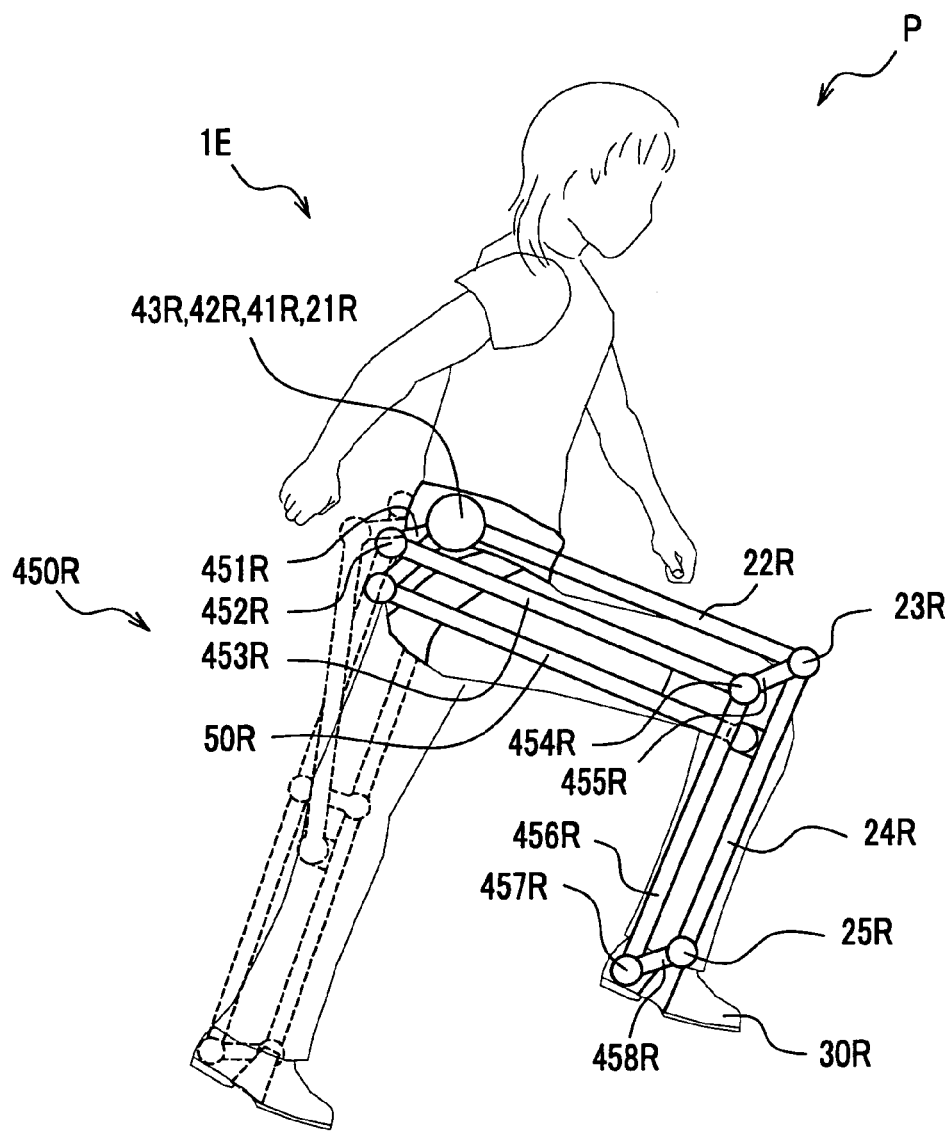
FIG. 22 is a side view illustrating an apparatus for assisting limb according to the present invention.
Figure 23:
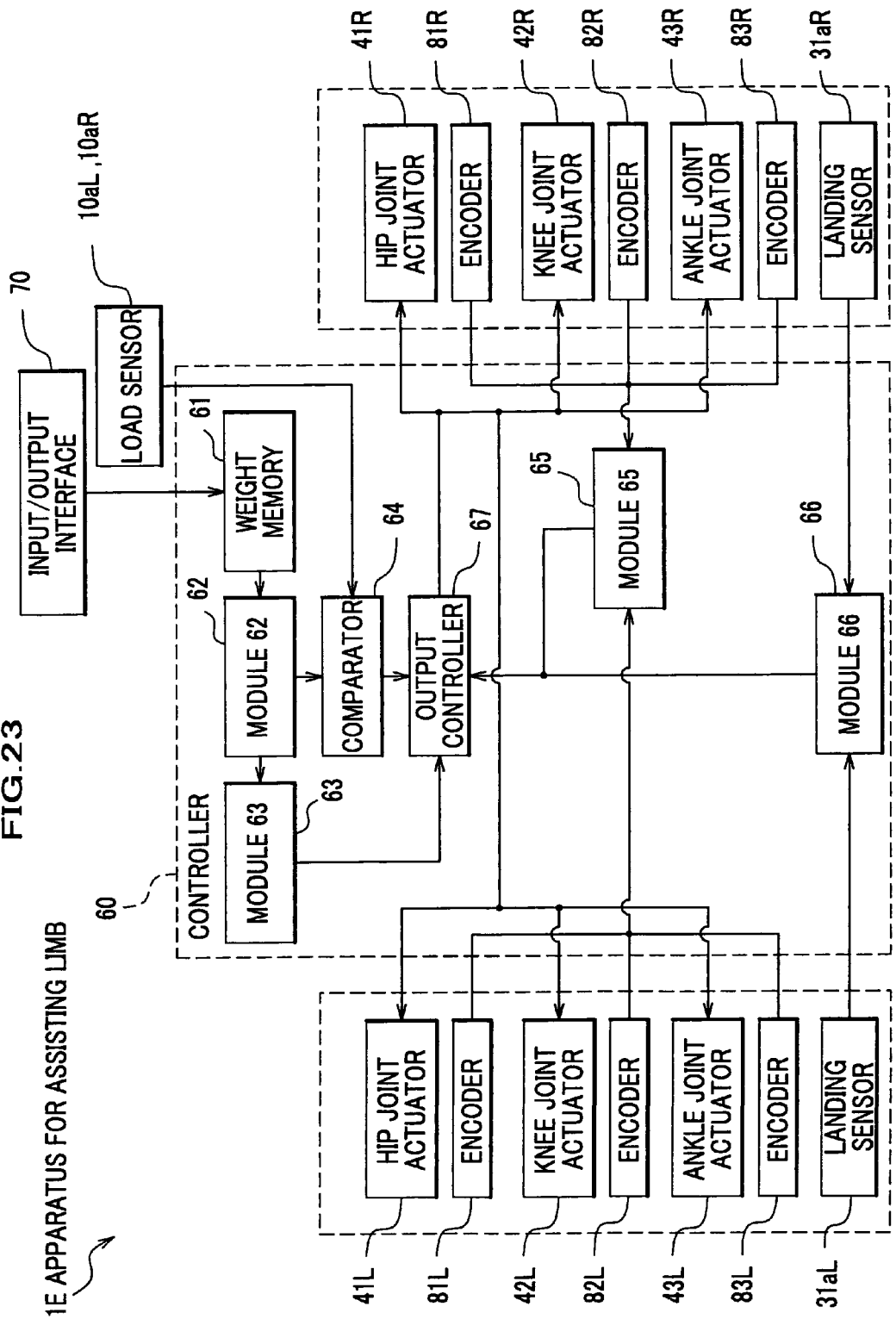
FIG. 23 is a functional block diagram showing an apparatus for assisting limb according to the present invention.

As shown in FIG. 22, an apparatus 1E according to the firth embodiment further includes an ankle joint actuator 43R and a link for ankle joint 450R.

The ankle joint actuator 43R is placed integrally and coaxially with a hip joint actuator 41R and a knee joint actuator 42R. The ankle joint actuator 43R, which has an electric motor and reduction gears, reduces output speed of the electric motor with the reduction gears, changing a relative position between a link for lower leg 24R and a foot attachment 30R. In other words, the ankle joint actuator 43R serves as an actuator for applying rotational torque to an ankle joint unit 25R so as to drive it. A base of the ankle joint actuator 43R is secured to an actuator mounting member 13R, and an output shaft of the ankle joint actuator 43R is secured to a distal portion of a first link 451R to be described later. In this connection, the geometrical relation of the ankle joint actuator 43R to these components is not limited to what has been described above.

An encoder (rotary encoder) 83R is attached to the ankle joint actuator 43R. The encoder 83R, which is an example of "behavior detector" in the appended claims, detects a rotational angle of the ankle joint actuator 43R as a data related to behavior of a link for lower limb 20R. The detected rotational angle is sent to a controller 60.

The link for ankle joint 450R includes a first link 451R, a first joint unit 452R, a second link 453R, a second joint unit 454R, a third link 455R, a fourth link 456R, a fourth joint unit 457R and a fifth link 458R. The first link 451R is coupled with the ankle joint actuator 43R. The second link 453R is coupled with the first link 451R via the first joint unit 452R. The third link 455R is coupled not only with the second link 453R via the second joint unit 454R, but also with a knee joint unit 23R. The fourth link 456R is coupled not only with the second link 453R via the second joint unit 454R, but also with a foot attachment 30R via the fourth joint unit 457R. The fifth link 458R is coupled with the fourth joint unit 457R and an ankle joint unit 25R. The fourth joint unit 457R is secured to the foot attachment 30R.

The ankle joint actuator 43R rotates the first link 451R, depressing or pulling the second link 453R in a direction of an axis of the upper leg. This makes the third link 455R rotate about the knee joint unit 23R, depressing or pulling the fourth link 456R in a direction of an axis of the lower leg. In this way, the fourth joint unit 457 attached to the foot attachment 30R is depressed or pulled, driving the ankle joint unit 25R.

When a shoe unit 31R has sufficient strength, it may be alternatively possible to eliminate the fifth link 458R.

In addition, it may be alternatively possible to adopt an arrangement that the link for ankle joint 450R is disposed inside of the drive unit 50R, on a closer side of a user P, instead of an example shown in FIG. 22, in which the link for ankle joint 450R is disposed outside of the drive unit 50R.

Furthermore, it may be possible to combine one of drive units 150R, 250R and 350R according to other embodiments with a link for ankle joint 450R.

A module 65 for detecting actuator state detects a state of the ankle joint unit 25L (25R) based on output from the encoder 83L (83R). The controller 60 is able to know a angle made by the link for lower leg 24L (24R) and the foot attachment 30L (30R) based on the output from the encoder 83L (83R).

An output controller 67 determines output to be generated by the ankle joint actuator 43L (43R), sending instruction to it.

Figure 24:
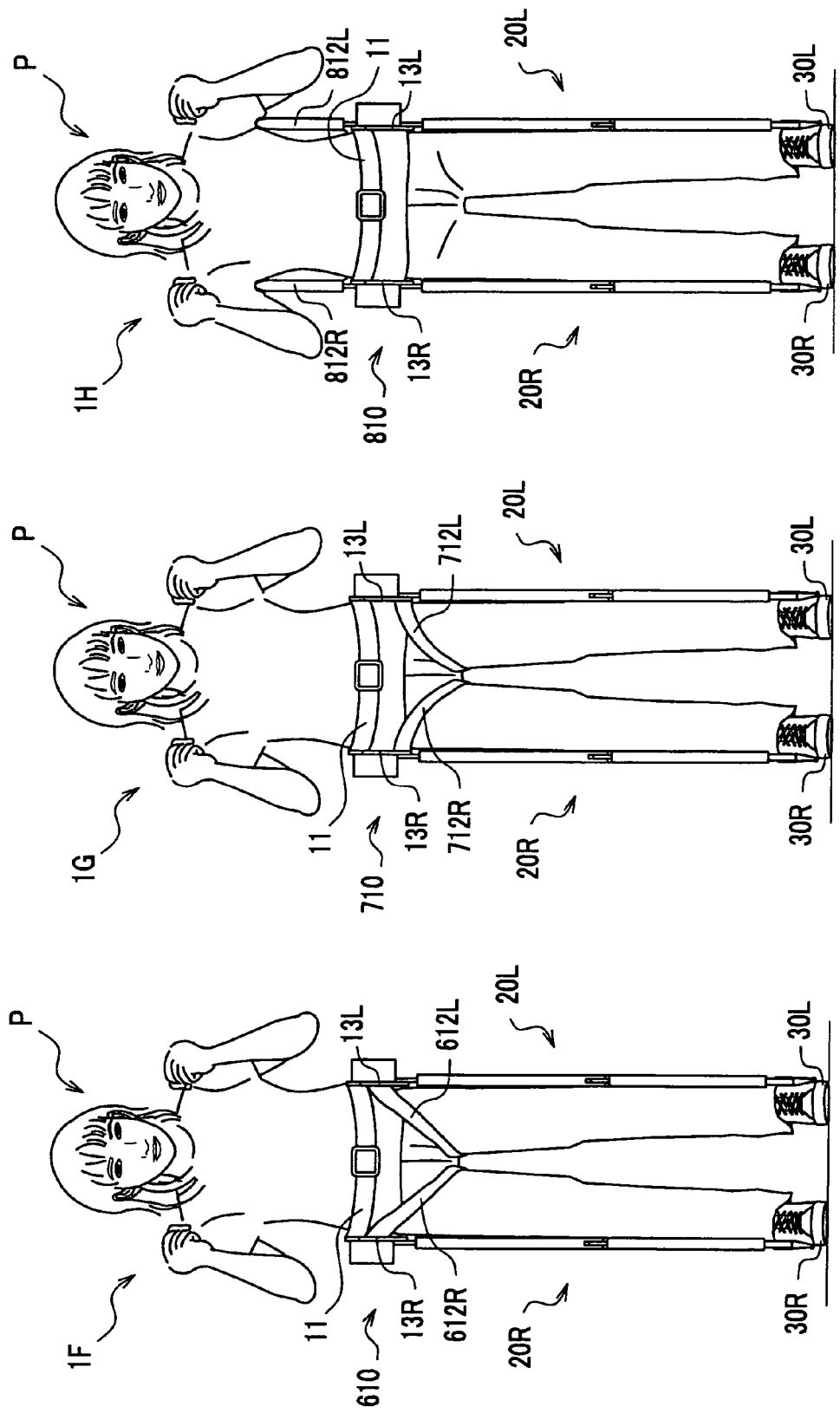
FIGS. 24A to 24C are each a schematic diagram illustrating a modification of a body attachment.

Description is now given of a modification to a body attachment, paying attention to differences from an apparatus 1A for assisting limb according to the first embodiment. In FIGS. 24A, 24B and 24C, a back pack BP is omitted.

As shown in FIG. 24A, a body attachment 610 of an apparatus 1F for assisting limb has a waist belt 11, actuator mounting members 13L and 13R and crotch belts 612L and 612R. The crotch belt 612L (612R), which is a cloth member worn around a crotch of a user P, is coupled with the actuator mounting member 13L (13R).

Figure 1:
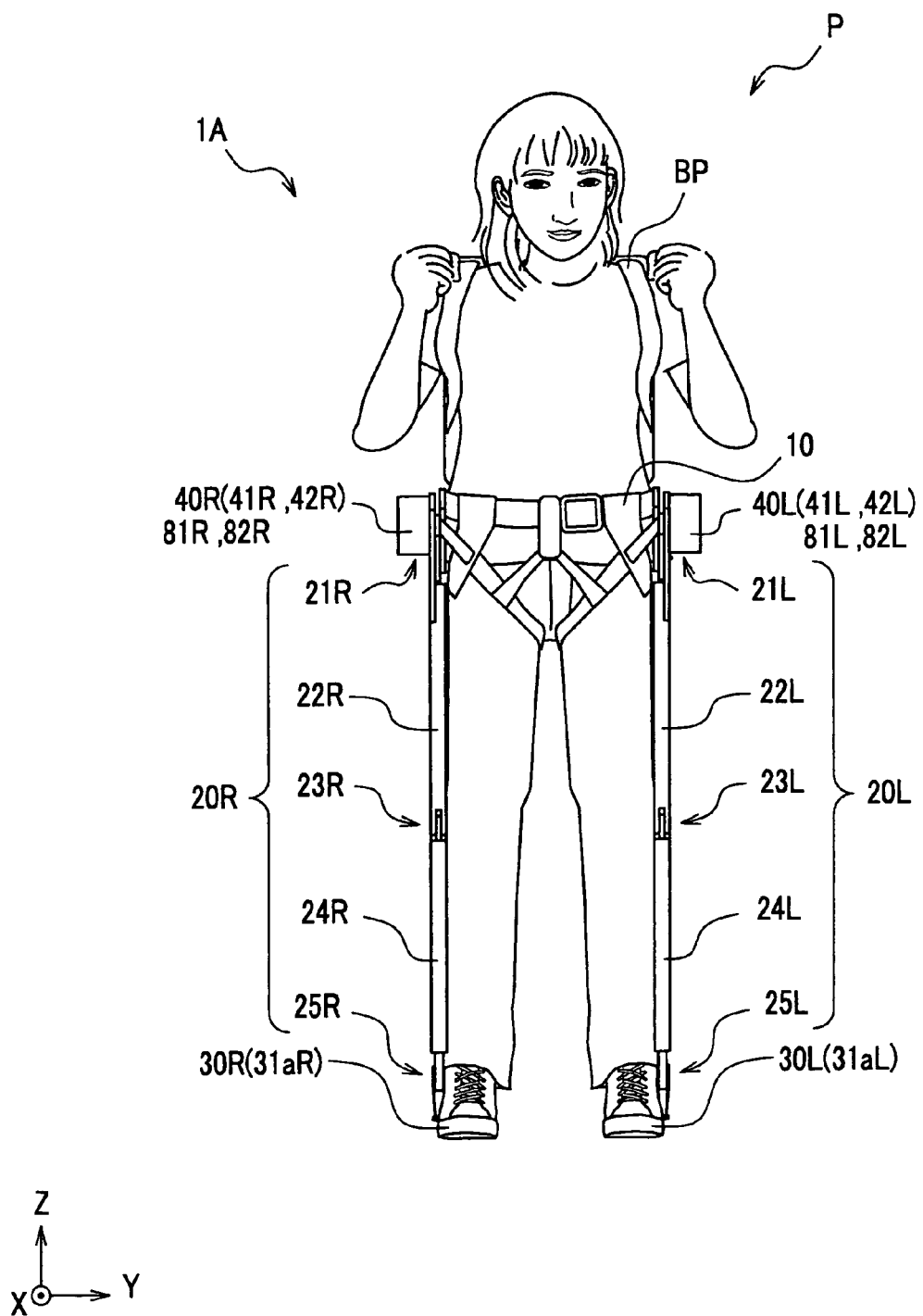
FIG. 1 is a front view illustrating an apparatus for assisting limb according to the present invention.
Figure 2:
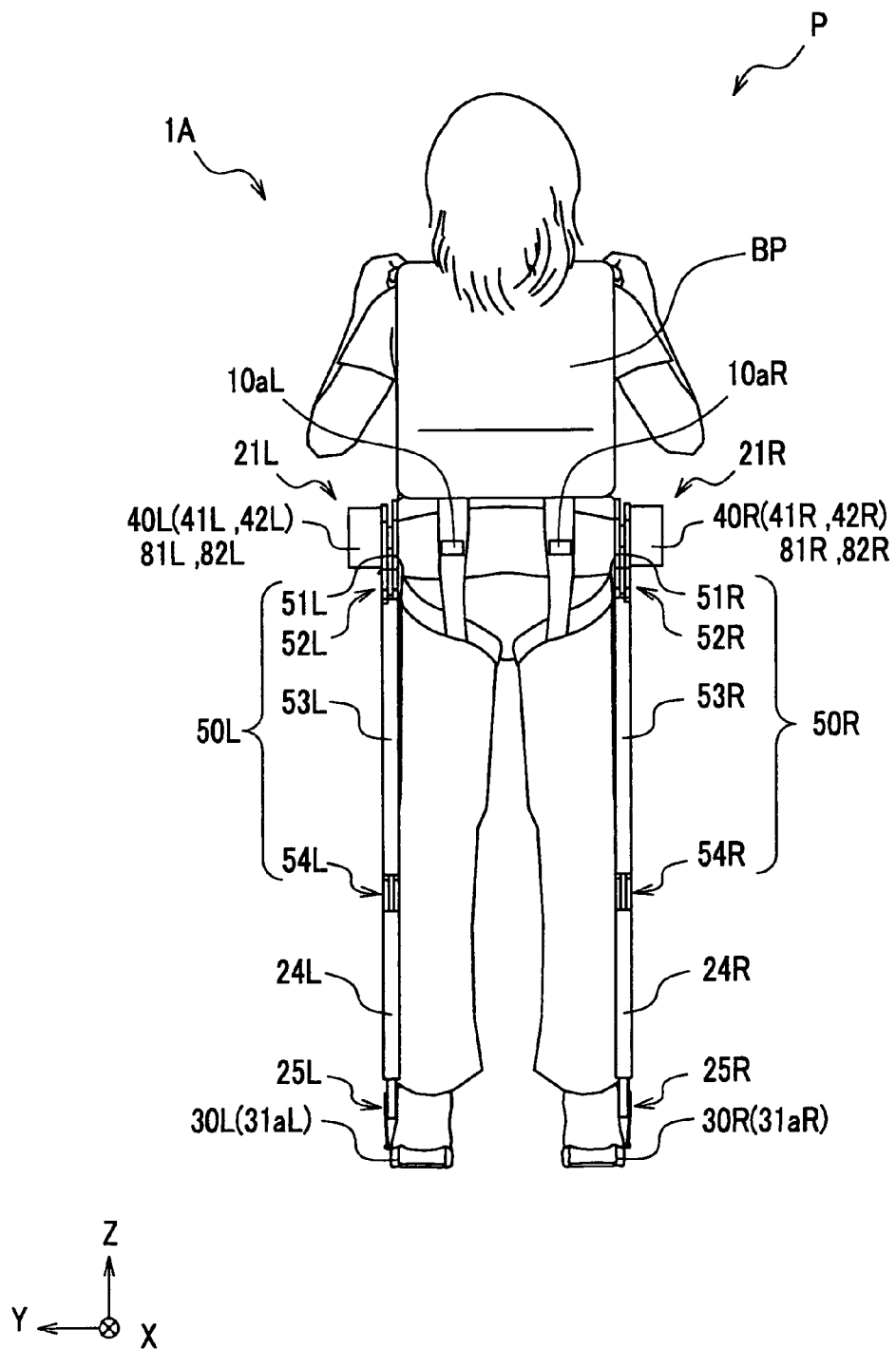
FIG. 2 is a rear view illustrating an apparatus for assisting limb according to the present invention.

The apparatus 1F, in which belts for a body attachment are simplified compared with the apparatus 1A shown in FIG. 1, has realized a weight reduction.

As shown in FIG. 24B, a body attachment 710 of an apparatus 1G for assisting limb has a waist belt 11, actuator mounting members 13L and 13R and upper leg belts 712L and 712R. The upper leg belt 712L (712R), which is a cloth member worn around an upper leg of a user P, is coupled with the actuator mounting member 13L (13R).

The apparatus 1G increases supporting capacity at upper legs of the user P compared with the apparatus 1F, relaxing a stress applied to a crotch of the user P.

As shown in FIG. 24C, a body attachment 810 of an apparatus 1H for assisting limb has a waist belt 11, actuator mounting members 13L and 13R and armpit support members 812L and 812R. The armpit support member 812L (812R) supporting a user P under his armpit is coupled with the actuator mounting member 13L (13R). The armpit support member 812L (812R), the actuator mounting member 13L (13R), a link for lower limb 20L (20R) and a foot attachment 30L (30R) are structurally designed to support a load imposed by the user P on the armpit support member 812L (812R).

The apparatus 1H is an example which is suitable for a user P who has trouble in being restricted around the upper legs or at the crotch due to illness or injury.

In addition to the modifications described above, it may be alternatively possible to adopt an arrangement in which an assist force is applied to a jaw of a user by an apparatus for assisting limb.

Description is given of a modification to a controller in view of differences from an apparatus 1A for assisting limb according to the first embodiment.

Figure 25:
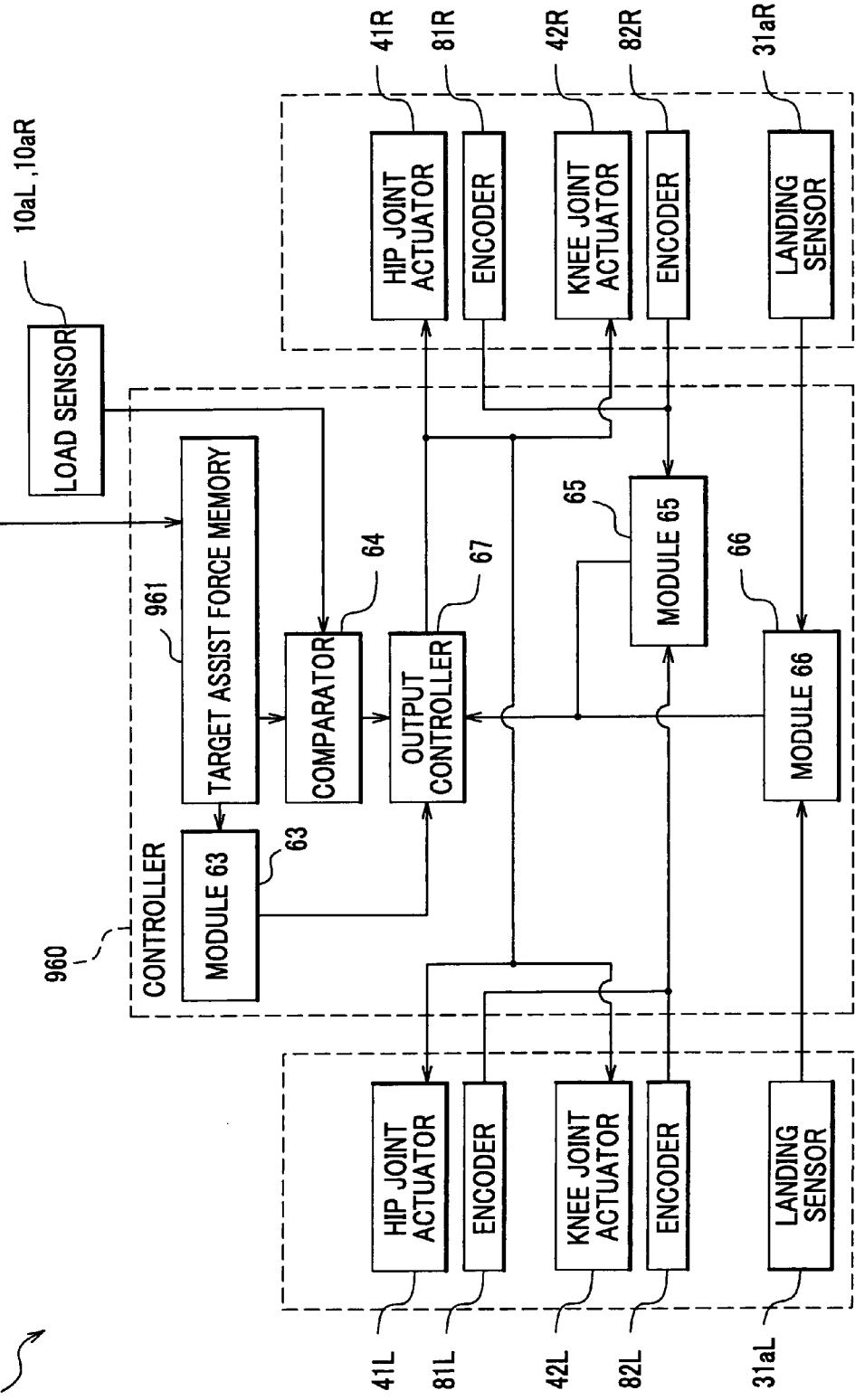
FIG. 25 is a block diagram depicting an example of modification of a controller.

As shown in FIG. 25, a controller 960 of an apparatus 1I for assisting limb has a target assist force memory 961 instead of a weight memory 61 and a module 62 for calculating target assist force.

The target assist force memory 961 stores a target assist force Fa, which is a predetermined value, 10 Kg for example. The target assist force memory 961 also stores a minimum target assist force Fa1, 9 Kg for example, and a maximum target assist force Fa2, 11 Kg for example, which are both set with respect to the target assist force Fa. The apparatus 11 executes in a functional flow calculation of initial torque and control for actuator torque according to the values described above.

Description is given of a modification in comparison with an apparatus 1E for assisting limb according to the fifth embodiment.

As shown in FIG. 26, an apparatus 1J for assisting limb has an architecture in which a knee joint actuator 42R and a drive unit 50R are eliminated.

The apparatus 1J is able to support movement for hip and ankle joints of a user P.

While description has been given of embodiments of the present invention with reference to the drawings, it will be apparent to one skilled in the art that the present invention can be modified without departing from the spirit and scope thereof.

It may be alternatively possible to employ only knee joint actuators so as to drive joint units by eliminating hip joint actuators, which leads to weight reduction and simplification of control for an apparatus for assisting limb.

It may be alternatively possible to dispose all actuators and links or at least one of them along inner sides of lower limbs of a user instead of the arrangement described above in the embodiments, in which all the actuators and links are disposed along outer sides of lower limbs of the user. It may be possible to apply an apparatus for assisting limb to upper limbs of a user. Furthermore, it may be possible that the apparatus assists ankle joints, elbow joints and wrist joints in addition to knee joins of a user.

It may be an alternative arrangement that an apparatus for assisting limb does not have a foot attachment and a distal portion of a link for lower leg lands on a floor. In this case, a foot of a user is coupled with a link for lower limb instead of a foot attachment, and a lower limb attachment is attached to one of an ankle, a lower leg, a knee and an upper leg. In this way, it may be possible to execute control for assist force, while an apparatus for assisting limb is synchronized with walking movement of the user and a landing sensor, which is attached to a sole of the user or a lower distal portion of the link for lower leg, detects a landed foot.

Figure 16:
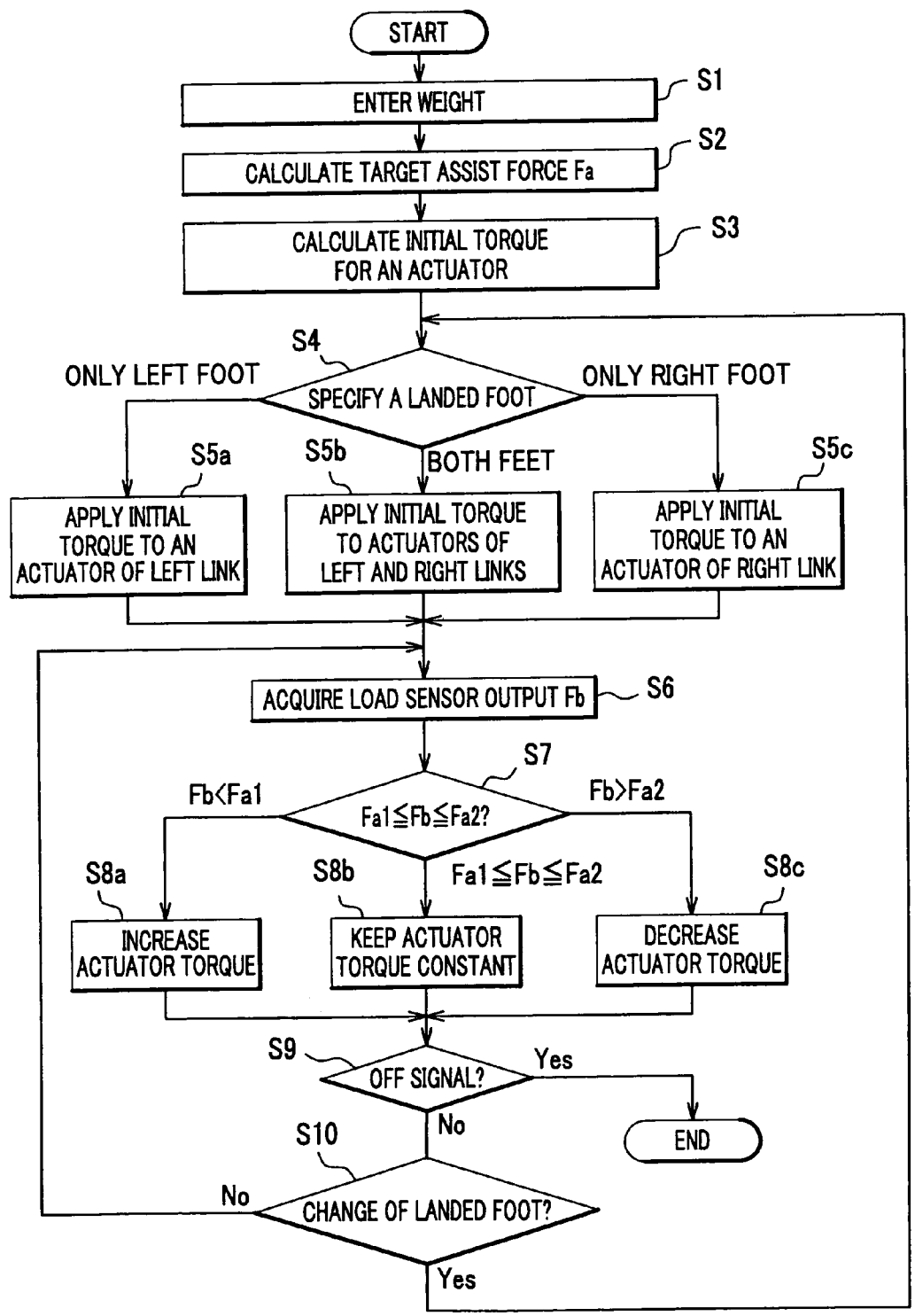
FIG. 16 is a flow chart showing an example of operation of an apparatus for assisting limb according to the present invention.

In the control flow shown in FIG. 16, an example has been described that a controller 60 executes processing according to a computer program stored in advance (limb assist program, also referred to as "lower limb assist program"). It may be alternatively possible to externally provide the computer program with a recording medium or via a network. The present invention includes the computer program, which executes a computer as a controller for an apparatus for assisting limb.

The present invention is not limited to an apparatus for assisting limb, which is intended for both lower limbs, but it may be alternatively possible to apply the apparatus to only one of left and right lower limbs. One example for this is that an apparatus is applied to only one lower limb of a user, which suffers physical weakness, so as to provide an assist force.

The present invention is not limited to a structural setup of a joint for an apparatus for assisting limb, which has been described with reference to the drawings. Shapes and materials of a body attachment and a foot attachment are not limited to what has been described above. It may also be possible to adopt an arrangement that an apparatus for assisting limb performs control for applying a driving force, which actively assists a user to walk. In this case, it may be possible to use a lower limb attachment which is attached to a lower leg of a user instead of a foot attachment.

Foreign priority document, JP2005-163864 filed on Jun. 3, 2005 is hereby incorporated by reference.

What is claimed is:

1. An apparatus for assisting a limb comprising:
a body attachment configured to be attached to a trunk of a user;
a link for an upper leg, the link for the upper leg configured to be placed alongside an upper leg of the user, and configured to be coupled with the body attachment;
a knee joint unit;
a link for a lower leg, the link for the lower leg configured to be placed alongside a lower leg of the user, and configured to be coupled with the link for the upper leg via the knee joint unit;
a lower limb attachment configured to be attached to one of the lower leg and a foot of the user, the lower limb attachment being coupled with the link for the lower leg;
a drive unit; and
a knee joint actuator configured to be placed in the body attachment so as to apply rotational torque to the knee joint unit via the drive unit;
a foot detector configured to detect one of a landed phase and a lifted phase of the foot of the user;
a controller configured to control the knee joint actuator,
wherein the controller is configured to perform drive control for the knee joint actuator so as to provide an assist force freeing the user from weight via the lower limb attachment when the foot is in the landed phase, and
wherein, when the foot detector detects a lifted phase, the controller terminates driving of the knee joint actuator.

2. An apparatus according to claim 1 further comprising:
wherein the lower limb attachment is configured to be attached to the foot of the user so that the lower limb attachment is able to land on the ground, and
wherein the controller is further configured to perform drive control for the link for lower leg, the link for upper leg, the drive unit and the body attachment.

3. An apparatus according to claim 2, wherein the assist force is equal to one of a predetermined value and a certain percentage of the weight of the user.

4. An apparatus according to claim 3 further comprising a load detector which detects a load imposed by the user via the body attachment on the link for upper leg, the link for lower leg, the drive unit and the lower limb attachment,
wherein the controller performs drive control for the knee joint actuator in a landed phase based on the load detected by the load detector.

5. An apparatus according to claim 4, wherein the assist force has a lower limit and an upper limit and wherein the controller performs drive control for the knee joint actuator in a landed phase based on the load detected by the load detector so that the assist force exists between the lower and upper limits.

6. An apparatus according to claim 2 further comprising a behavior detector configured to detect a signal indicative of behavior for the link for upper leg and the link for lower leg, wherein the controller performs drive control for the knee joint actuator based on the signal detected by the behavior detector.

7. An apparatus according to claim 4, wherein a first portion at which the assist force is applied to the user via the link for upper leg and a second portion to which the load of the user is applied in the body attachment are positioned so that the fist and second portions are substantially included in a common vertical plane.

8. An apparatus according to claim 1 further comprising:
a hip joint unit; and
a hip joint actuator;
wherein the body attachment is coupled with the link for upper leg via the hip joint unit, and
wherein the hip joint actuator is integrally installed with the knee joint actuator in the body attachment so as to apply rotational torque to the hip joint unit.

9. An apparatus according to claim 8 further comprising:
wherein the controller configured to control hip joint actuator,
wherein the lower limb attachment is configured to be attached to the foot of the user so that the lower limb attachment is able to land on the ground, and
wherein the controller performs drive control for the knee joint actuator and the hip joint actuator so as to provide an assist force freeing the user from weight via the lower limb attachment in a landed phase, the link for lower leg, the link for upper leg, the drive unit and the body attachment.

10. An apparatus according to claim 9, wherein when the foot detector detects a lifted phase, the controller terminates driving of at least one of the knee joint actuator and the hip joint actuator.

11. An apparatus according to claim 9, wherein when the foot detector detects a lifted phase, the controller performs drive control for the hip joint actuator so as to assist a swing for the upper leg of the user.

12. An apparatus according to claim 9, wherein the assist force is equal to one of a predetermined value and a certain percentage of the weight of the user.

13. An apparatus according to claim 12 further comprising a load detector which detects a load imposed by the user via the body attachment on the link for upper leg, the link for lower leg, the drive unit and the lower limb attachment,
wherein the controller performs drive control for the knee joint actuator and the hip joint actuator in a landed phase based on the load detected by the load detector.

14. An apparatus according to claim 13, wherein the assist force has a lower limit and an upper limit and wherein the controller performs drive control for the knee joint actuator and the hip joint actuator based on the load detected by the load detector so that the assist force exists between the lower and upper limits.

15. An apparatus according to claim 9 further comprising a behavior detector configured to detect a signal indicative of behavior for the link for upper leg and the link for the lower leg, wherein the controller performs drive control for the knee joint actuator and the hip joint actuator based on the signal detected by the behavior detector.

16. An apparatus according to claim 13, wherein a first portion at which the assist force is applied to the user via the link for upper leg and a second portion to which the load of the user is applied in the body attachment are positioned so that the fist and second portions are substantially included in a common vertical plane.

17. An apparatus according to claim 1, wherein the drive unit comprises a link for knee joint configured to drive the knee joint unit and the link is placed alongside with the link for upper leg.

18. An apparatus according to claim 1, wherein the drive unit transmits a driving force by one of a belt, wires and a combination of a shaft and gears so as to apply rotational torque to the knee joint unit.

19. An apparatus according to claim 17 further comprising:

an ankle joint unit;

a link for ankle joint configured to drive the ankle joint unit; and an ankle joint actuator, wherein the lower limb attachment is coupled with the link for lower leg via the ankle joint unit, and wherein the ankle joint actuator is integrally installed with the knee joint actuator in the body attachment so as to apply rotational torque to the ankle joint unit via the link for ankle joint.

* * * * *